US012264402B2

(12) United States Patent
Mariano et al.

(10) Patent No.: US 12,264,402 B2
(45) Date of Patent: *Apr. 1, 2025

(54) CHLOR-ALKALI AND CARBON MONOXIDE ELECTROLYZER INTEGRATION

(71) Applicant: Dioxycle, Bordeaux (FR)

(72) Inventors: Ruperto G Mariano, South San Francisco, CA (US); Joshua A. Rabinowitz, San Francisco, CA (US); Sarah Lamaison, Paris (FR); David Wakerley, Paris (FR)

(73) Assignee: Dioxycle, Bordeaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/237,897

(22) Filed: Aug. 25, 2023

(65) Prior Publication Data

US 2024/0425995 A1 Dec. 26, 2024

Related U.S. Application Data

(60) Provisional application No. 63/521,878, filed on Jun. 20, 2023.

(51) Int. Cl.
*C25B 3/25* (2021.01)
*C01B 7/01* (2006.01)
(Continued)

(52) U.S. Cl.
CPC .............. *C25B 3/25* (2021.01); *C01B 7/012* (2013.01); *C07C 17/02* (2013.01); *C07C 17/156* (2013.01);
(Continued)

(58) Field of Classification Search
CPC .... C25B 3/01; C25B 3/03; C25B 3/05; C25B 3/07; C25B 3/09; C25B 3/11; C25B 3/21;
(Continued)

(56) References Cited

U.S. PATENT DOCUMENTS

| | | | | |
|---|---|---|---|---|
| 4,749,453 A | * | 6/1988 | Harris ................. | H01M 8/0656 205/516 |
| 10,329,676 B2 | | 6/2019 | Kaczur et al. | |

(Continued)

FOREIGN PATENT DOCUMENTS

| | | |
|---|---|---|
| AU | 2021322122 A1 | 3/2023 |
| EP | 3427320 A1 | 1/2019 |

(Continued)

OTHER PUBLICATIONS

Rippati et al. "Carbon Monoxide Gas Diffusion Electrolysis that Produces Concentrated C2 Products with High Single-Pass Conversion" Joule, vol. 3, Issue 1, 2019, 240-256 (Year: 2018).*

(Continued)

*Primary Examiner* — Luan V Van
*Assistant Examiner* — Alexander R. Parent
(74) *Attorney, Agent, or Firm* — Daylight Law, P.C.

(57) ABSTRACT

Integrations of carbon monoxide electrolyzers and chlor-alkali electrolyzers are disclosed herein. The disclosed integrations include novel process chains for the valorization of oxocarbons into hydrochloric acid, vinyl chloride, vinyl acetate, ethylene oxide, and other useful chemicals. The disclosed integrations further include novel ways to operate the electrolyzers in tandem to increase the efficiency of both reactors. This disclosure also includes novel ways to balance the operation of both electrolyzers to assure they are operating at an optimal level to take advantage of the benefits of the disclosed integrations.

25 Claims, 17 Drawing Sheets

(51) Int. Cl.

| | |
|---|---|
| *C07C 17/02* | (2006.01) |
| *C07C 17/156* | (2006.01) |
| *C07C 17/158* | (2006.01) |
| *C07C 17/358* | (2006.01) |
| *C25B 1/02* | (2006.01) |
| *C25B 1/04* | (2021.01) |
| *C25B 1/34* | (2006.01) |
| *C25B 3/03* | (2021.01) |
| *C25B 3/07* | (2021.01) |
| *C25B 15/02* | (2021.01) |
| *C25B 15/08* | (2006.01) |

(52) U.S. Cl.
CPC .......... *C07C 17/158* (2013.01); *C07C 17/358* (2013.01); *C25B 1/04* (2013.01); *C25B 1/34* (2013.01); *C25B 3/03* (2021.01); *C25B 3/07* (2021.01); *C25B 15/02* (2013.01); *C25B 15/083* (2021.01); *C25B 1/02* (2013.01)

(58) Field of Classification Search
CPC .. C25B 3/25; C25B 3/26; C25B 15/08; C25B 15/083; C25B 1/34; C25B 15/087; C25B 15/031; C25B 1/46; C25B 3/00; C01B 7/012; C01B 1/27; C01C 1/164; C01C 1/16; C01C 1/18; C01C 1/24; Y10T 436/12
See application file for complete search history.

(56) References Cited

U.S. PATENT DOCUMENTS

| | | | |
|---|---|---|---|
| 11,512,403 B2 * | 11/2022 | Kuhl | ............ C25B 1/04 |
| 2011/0077366 A1 | 3/2011 | Petitjean et al. | |
| 2014/0158518 A1 | 6/2014 | Benje et al. | |
| 2017/0121831 A1 * | 5/2017 | Kaczur | ............ C25B 1/46 |
| 2022/0136119 A1 * | 5/2022 | Flanders | ............ C25B 3/26 |
| | | | 435/71.1 |
| 2022/0153656 A1 | 5/2022 | Flanders et al. | |
| 2022/0170166 A1 * | 6/2022 | Li | ............ C25B 15/087 |
| 2022/0177399 A1 | 6/2022 | Klemt et al. | |

FOREIGN PATENT DOCUMENTS

| | | |
|---|---|---|
| WO | 2008155394 A2 | 12/2008 |
| WO | 2016149507 A1 | 9/2016 |
| WO | 2017216272 A1 | 12/2017 |
| WO | 2022031726 A2 | 2/2022 |
| WO | 2023081846 A1 | 5/2023 |

OTHER PUBLICATIONS

O'Brien et al. (Handbook of Chlor-Alkali Technology, vol. 1: Fundamentals "Chapter 9: Product Handling" Springer New York, NY 2007 eBook ISBN 978-0-306-48624-1) (Year: 2007).*

O'Brien et al. (Handbook of Chlor-Alkali Technology, vol. 1: Fundamentals "Chapter 7: Brine Preparation and Treatment" Springer New York, NY 2007 eBook ISBN 978-0-306-48624-1) (Year: 2007).*

Ripatti et al. ("Carbon Monoxide Gas Diffusion Electrolysis that Produces Concentrated C2 Products with High Single-Pass Conversion" Joule, vol. 3, Issue 1, 2019, 240-256'') (Year: 2019).*

Ramdin et al. ("High-Pressure Electrochemical Reduction of CO2 to Formic Acid/Formate: Effect of pH on the Downstream Separation Process and Economics" Ind. Eng. Chem. Res. 2019, 58, 22718-22740) (Year: 2019).*

EPA (Water Treatment Chemical Supply Chain Profiles "Sodium Hydroxide Supply Chain" Mar. 2023) (Year: 2023).*

Yan et al. ("Synergy of Cu/C3N4 Interface and Cu Nanoparticles Dual Catalytic Regions in Electrolysis of CO to Acetic Acid" Angew. Chem. Int. Ed. 2023, 62, e202301507) (Year: 2023).*

Khursheed et al. ("Visualization and Quantification of Sodium Chloride Formed during the Titration of Hydrochloric Acid with Sodium Hydroxide: An Extension to the Learning Outcomes During Acid-Base Titrations" J. Chem. Ed. 2024 2118-2123) (Year: 2024).*

F. Türk et al., (2020). Reactive Extraction of Monocarboxylic Acids (Formic, Acetic, and Propionic) Using Tributyl Phosphate in Green Solvents (Cyclopentyl Methyl Ether and 2-Methyltetrahydrofuran). Journal of Chemical & Engineering Data.

H.S. Yun et al. (2017). Simultaneous Sodium Hydroxide Production by Membrane Electrolysis and Carbon Dioxide Capture. Chemical Engineering & Technology, 40, 2204-2211.

T. Brinkmann et al. Best Available Techniques (BAT) Reference Document for the Production of Chlor-alkali. Industrial Emissions Directive 2010/75/EU (Integrated Pollution Prevention and Control). EUR 26844. Luxembourg (Luxembourg): Publications Office of the European Union; 2014. JRC91156.

H. Ma et al., (2020). Critical Review of Catalysis for Ethylene Oxychlorination. ACS Catalysis.

I. Moussallem et al. (2008). Chlor-alkali electrolysis with oxygen depolarized cathodes: history, present status and future prospects. Journal of Applied Electrochemistry, 38, 1177-1194.

Non-Final Office Action dated Nov. 21, 2023 from U.S. Appl. No. 18/238,462, 32 pages.

Notice of Allowance dated Oct. 30, 2024 from U.S. Appl. No. 18/238,462, 16 pages.

International Search Report and Written Opinion from International Application No. PCT/IB2024/056007 dated Feb. 3, 2025, 20 pages.

M. Ramdin et al. (2021). Electroreduction of CO2/CO to C2 Products: Process Modeling, Downstream Separation, System Integration, and Economic Analysis. Industrial & Engineering Chemistry Research, 60, 17862-17880.

* cited by examiner

CHLOR-ALKALI AND CARBON MONOXIDE ELECTROLYZER INTEGRATION

CROSS REFERENCE TO RELATED APPLICATIONS

This application claims the benefit of U.S. Provisional Application No. 63/521,878, filed on Jun. 20, 2023, which is incorporated by reference herein in its entirety for all purposes.

BACKGROUND

There is an urgent need to develop technologies which make the capture or valorization of carbon dioxide ($CO_2$) more economical in highly emitting sectors such as industrial chemical production. Furthermore, there is an urgent need to reduce emissions related to the production of useful fuels and chemicals in our society and to find alternative ways to produce such fuels sustainably instead of relying on fossil resource extraction and processing for their production. Accordingly, technologies that both generate useful fuels and chemicals, while at the same time using oxocarbon feedstocks that would otherwise have been emitted into the atmosphere, are critically important because they both generate useful chemicals without additional emissions and mitigate the impact of the emission sources from which they capture oxocarbons. Furthermore, the economic value of the useful chemicals can offset the cost of oxocarbon capture and conversion, adding further economic incentives to prevent the emission of greenhouse gases into the atmosphere.

SUMMARY

This disclosure relates to carbon monoxide (CO) electrolyzers and more specifically to the integration of CO electrolyzers with chlor-alkali electrolyzers. The disclosed integrations include novel process chains for the valorization of oxocarbons into hydrochloric acid, vinyl chloride, vinyl acetate, ethylene oxide, and other useful chemicals. The disclosed integrations further include novel ways to operate the electrolyzers in tandem to increase the efficiency of both reactors. This disclosure also includes novel ways to balance the operation of both electrolyzers to assure they are operating at an optimal level to take advantage of the benefits of the disclosed integrations.

CO electrolyzers offer numerous opportunities to valorize oxocarbons by either directly valorizing CO or by indirectly valorizing $CO_2$ or other oxocarbons that are first converted into CO. The operation of CO electrolyzers that can be used for these purposes and that can be used in accordance with the embodiments disclosed herein are disclosed in U.S. patent application Ser. No. 18/111,631 as filed on Feb. 20, 2023, which is incorporated by reference herein in its entirety for all purposes. These CO electrolyzers offer numerous benefits in terms of their efficiency and ability to valorize CO into useful chemicals. However, the operation of CO electrolyzers exhibit certain drawbacks that can be alleviated through integrative operation with a chlor-alkali electrolyzer as disclosed herein.

One problem with CO electrolyzers is that basic electrolyte streams may be necessary to ensure effective conversion of the CO into useful chemicals. The basic electrolyte streams can be aqueous alkaline streams which operate as the anolyte or catholyte of the electrolyzer such that any useful products generated at the corresponding electrode of the electrolyzer will be mixed with the basic stream and may be difficult to separate from the basic stream. Particularly, certain useful chemicals in the form of ionically charged or miscible products, such as, but not limited to carboxylates such as acetate, alcohols such as ethanol and propanol, and organic acids such as propionic acid, can require large additional energy requirements to neutralize or evaporate them from the stream. These separation requirements may ultimately add prohibitive cost to the conversion process and render it infeasible from an energetic perspective. For this reason, cost-effective means to separate these highly valuable organic species from basic streams will improve the economic viability of environmentally beneficial emission-valorizing systems. As disclosed below, integration with a chlor-alkali electrolyzer can provide ways to efficiently remove such useful chemicals from the output stream of the CO electrolyzer.

Another problem with CO electrolyzers is the consumption of hydroxide in the electrolyte of the CO electrolyzer which leads to reduced performance of the electrolyzer overtime. For example, during the cathodic electrosynthesis of carboxylate in an alkaline electrolyte in a CO electrolyzer, the overall process leads to the stoichiometric consumption of one equivalent of hydroxide for every equivalent of carboxylate produced because of charge balance. Additional carboxylate is produced when alcohols such as ethanol and propanol are oxidized to acetate and propionate at the anode, leading to further consumption of hydroxide. Further losses in the hydroxide content of the electrolyte can arise from the transport, generation, or dialysis of hydroxide to or at the cathode and into the cathode trap, where it is physically segregated from the electrolyte. The consumption of hydroxide or its inefficient transport to the anode during CO electrolysis leads to a lower electrolyte pH at steady-state relative to initial conditions, which leads to a decline in performance because the energy efficiency of earth-abundant anodes for CO electrolysis is higher in strongly alkaline media. Lower electrolyte pH also leads to the dissolution of labile species necessary for high performance from the anode (e.g., Fc) possibly followed by their redeposition on the cathode, which leads to an increase in cell voltage and losses in selectivity for valuable products at the cathode. The consumption of hydroxide also increases cell voltage and energy consumption by lowering solution conductivity, because the specific molar conductivity of acetate is lower than that of hydroxide. These issues have heretofore not been obvious to address because CO electrolysis systems have only recently reached high productivities such that large amounts of hydroxide are converted during electrolysis. As disclosed below, integration with a chlor-alkali electrolyzer can provide ways to preserve the hydroxide content of a CO electrolyzer by refreshing the electrolyte.

Regardless of whether a given organic species needs to be harvested as a useful chemical or is unacceptably lowering the pH of the electrolyte, its removal from the electrolyte is beneficial for other reasons related to the performance of the CO electrolyzer. For example, in addition to lowering solution pH by consuming hydroxide, many of the useful chemicals that can be generated by a CO electrolyzer, including alkali metal acetates and propionates, and acetic acid and propionic acid, are all amphiphilic substances which degrade the performance of certain CO electrolyzers. When amphiphilic substances are generated during CO electrolysis and build up in the CO electrolyzer, the substances degrade the hydrophobicity of the cathode and thus impede the efficient transport and conversion of CO. It is thus of interest to actively remove these species from the electrolyte to preserve the rate of CO transport and conversion. Under some conditions, alkali metal carboxylates can also precipitate as solids, leading to impeded gaseous, ionic, and electronic transport and thus reducing overall efficiency.

Specific embodiments disclosed herein use the combination of a chlor-alkali electrolyzer with a CO electrolyzer in order to reduce the energy demand of producing valuable chemicals from a CO electrolyzer and address the drawbacks mentioned above. A chlor-alkali electrolyzer is an electrolyzer used to produce chlorine and an alkali metal hydroxide (e.g., sodium hydroxide) through the electrolysis of a solution of an alkali metal and chloride (e.g., sodium chloride). Sodium hydroxide is also referred to as caustic soda in the industry. Chlor-alkali electrolyzers can include an oxygen depolarized cathode which is a porous structure that facilitates a three-phase interface process, where oxygen gas is reduced in the presence of liquid water on the surface of a solid electrocatalyst. To obtain highly pure alkali metal hydroxide solutions from the process, the inlet of an oxygen depolarized chlor-alkali electrolyzer cathode can be scrubbed because $CO_2$ reacts with the electrolyte to produce carbonate ($CO_3^{2-}$).

In specific embodiments of the invention, a method is provided. The method comprises generating a volume of chlorine gas using a chlor-alkali reactor, generating a volume of dihydrogen using a carbon monoxide electrolyzer, separating the volume of dihydrogen from an output stream of the carbon monoxide electrolyzer and generating a volume of hydrochloric acid using a hydrochloric acid reactor, the volume of dihydrogen, and the volume of chlorine gas.

In specific embodiments of the invention, another method is provided. The method comprises generating a volume of a metal hydroxide using a metal salt and a chlor-alkali reactor and generating an output stream using a carbon monoxide electrolyzer. The metal hydroxide is an electrolyte of the carbon monoxide electrolyzer. The method also comprises supplying the volume of metal hydroxide to the carbon monoxide electrolyzer to be used as the electrolyte of the carbon monoxide electrolyzer and acidifying the output stream of the carbon monoxide electrolyzer. The output stream includes the electrolyte. The metal hydroxide in the output stream is converted into a volume of the metal salt. The method further comprises supplying the volume of metal salt to the chlor-alkali reactor to be used to generate a volume of chlorine gas.

In specific embodiments of the invention, another method is provided. The method comprises generating a volume of chlorine gas using a chlor-alkali reactor, generating a volume of acetate using a carbon monoxide electrolyzer, generating a volume of hydrochloric acid using a hydrochloric acid reactor, monitoring a rate of production of the acetate, and changing a rate of production of the volume of hydrochloric acid based on the rate of production of the volume of acetate, wherein the rate of production of the volume of hydrochloric acid is increased when the rate of production of the acetate increases, and wherein the rate of production of the volume of hydrochloric acid is decreased when the rate of production of the acetate decreases.

In specific embodiments of the invention, a method for generating vinyl chloride is provided. The method comprises generating a volume of chlorine gas using a chlor-alkali reactor, generating a volume of ethylene using a carbon monoxide electrolyzer, generating a volume of ethylene dichloride using an ethylene chlorination reactor, the volume of chlorine gas, and the volume of ethylene, and generating a volume of vinyl chloride using an ethylene dichloride to vinyl chloride reactor and the volume of ethylene dichloride.

In specific embodiments of the invention, a method for generating vinyl acetate is provided. The method comprises generating a volume of chlorine gas using a chlor-alkali reactor, generating a volume of ethylene and a volume of oxygen using a carbon monoxide electrolyzer, and acidifying an output stream of the carbon monoxide electrolyzer using the volume of hydrochloric acid. The output stream includes a volume of carboxylates. The acidifying of the output stream of the carbon monoxide electrolyzer converts the volume of carboxylates to a volume of carboxylic acid. The method further comprises distilling a volume of acetic acid from the volume of carboxylic acid and generating a volume of vinyl acetate using a vinyl acetate synthesis reactor, the volume of acetic acid, the volume of ethylene, and the volume of oxygen.

In specific embodiments of the invention, a method for generating ethylene oxide is provided. The method comprises generating a volume of ethylene and a volume of oxygen using a carbon monoxide electrolyzer, generating a volume of ethylene oxide and a volume of carbon dioxide using an ethylene oxide synthesis reactor, the volume of oxygen, and the volume of ethylene, converting the volume of carbon dioxide to a second volume of carbon monoxide, and supplying the second volume of carbon monoxide to the carbon monoxide electrolyzer.

BRIEF DESCRIPTION OF THE DRAWINGS

The accompanying drawings illustrate various embodiments of systems, methods, and embodiments of various other aspects of the disclosure. A person with ordinary skills in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

In the block diagrams which illustrate electrolyzer integrations, lines represent fluid connections that fluidly connect the functional blocks they connect. The connection of a line to a block can be referred to as an input to that block. The connection of a line extending from a block can be referred to as an output of that block. The term "fluid connection" as used herein is not meant to be constrained to a single connection between two blocks. Instead, that term is meant to refer to a fluid connection which can extend through multiple functional blocks. Furthermore, the term "output stream" is meant to refer to a stream of one or more chemicals which are traveling through a fluid connection in a given direction and the term can continue to refer to that stream even if component chemicals of that stream are divided off (e.g., if carbon dioxide is separated from an output stream, the remainder can still be referred to as an output stream).

DETAILED DESCRIPTION

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Methods and systems for the integration of CO electrolyzers and chlor-alkali electrolyzers in accordance with the summary above are disclosed in detail herein. The methods and systems disclosed in this section are nonlimiting embodiments of the invention, are provided for explanatory purposes only, and should not be used to constrict the full scope of the invention. It is to be understood that the disclosed embodiments may or may not overlap with each other. Thus, part of one embodiment, or specific embodiments thereof, may or may not fall within the ambit of another, or specific embodiments thereof, and vice versa. Different embodiments from different aspects may be combined or practiced separately. Many different combinations and sub-combinations of the representative embodiments shown within the broad framework of this invention, that may be apparent to those skilled in the art but not explicitly shown or described, should not be construed as precluded.

Figure 1:
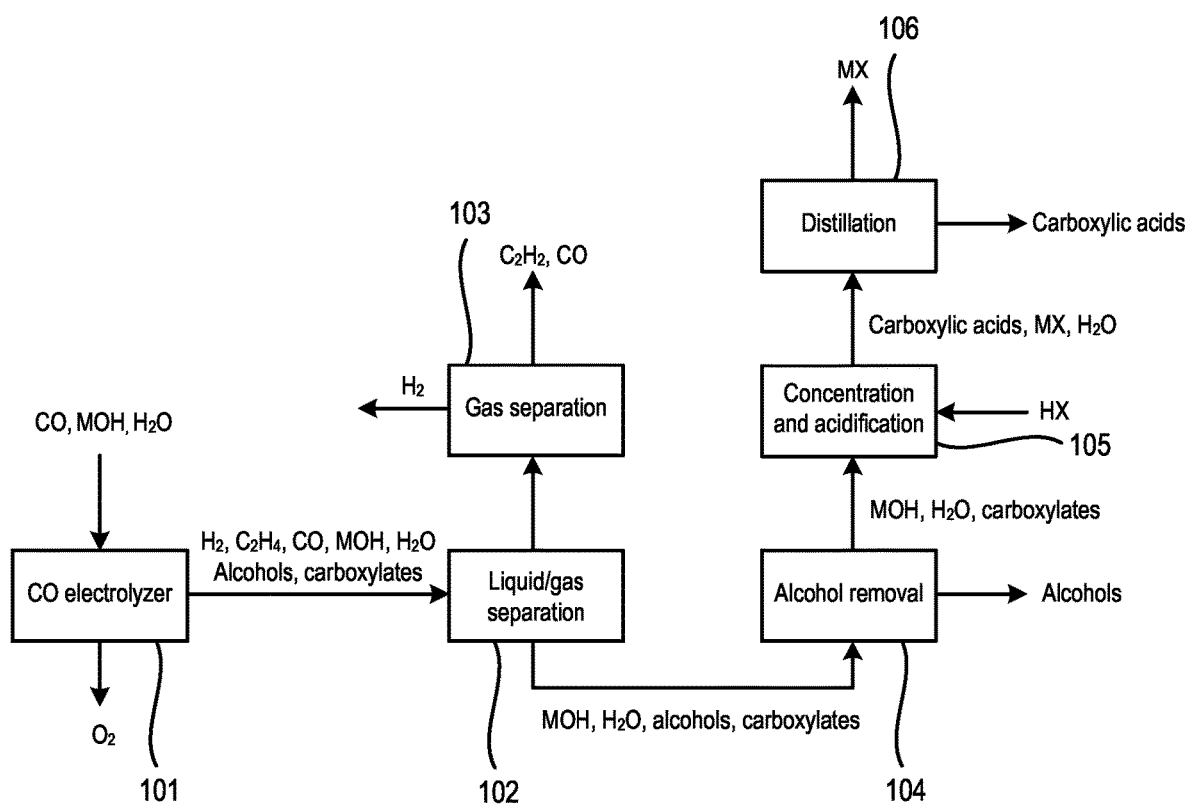
FIG. 1 illustrates a CO electrolyzer process chain in accordance with specific embodiments of the inventions disclosed herein.

A CO electrolyzer process chain is illustrated in FIG. 1. It is composed of a CO electrolyzer 101 with downstream subunits to allow for separation and purification of the output stream, and upstream components to provision gas, water, and alkaline equivalents required to operate the electrolyzer. The input gas can include carbon monoxide which is supplied to the cathode of the CO electrolyzer and is used to produce various useful chemicals such as but not limited to carboxylates such as acetate, alcohols such as ethanol and propanol, organic acids such as propionic and acetic acid, dihydrogen, ethylene, and propionate. The electrolyte of the CO can include, as described in the summary above, a metal (M) hydroxide (MOH). Depending upon how the CO electrolyzer is operated, it can also produce purified dioxygen and dihydrogen gas. The downstream subunits include a liquid/gas separation unit 102 to recover gaseous products from the output stream departing the electrolyzer, a gas separation unit 103 placed downstream of the gas/liquid separation unit, and an alcohol removal system 104 placed downstream of the liquid/gas separation subunit to recover alcohol products from the CO electrolyzer. The alcohol removal system can use methods such as but not limited to distillation, adsorption, or solvent based extraction to separate and recover the alcohol products. The downstream subunits further include a concentration and/or acidification subunit 105, downstream of the alcohol removal subunit, to convert the metal hydroxide and carboxylate products into carboxylic acid, co-producing a metal salt solution in water. The acidification subunit takes as an input an acid (HX), such as hydrochloric acid HCl, which is converted into a metal salt (MX) through the acidification of the input carboxylates and MOH. A liquid product separation method such as but not limited to distillation 106 and/or solvent based extraction can be used to separate the carboxylic acid from the aqueous salt solution. The overall illustrated process chain takes CO and MOH as an input and outputs MX and the illustrated useful chemicals.

Figure 2:
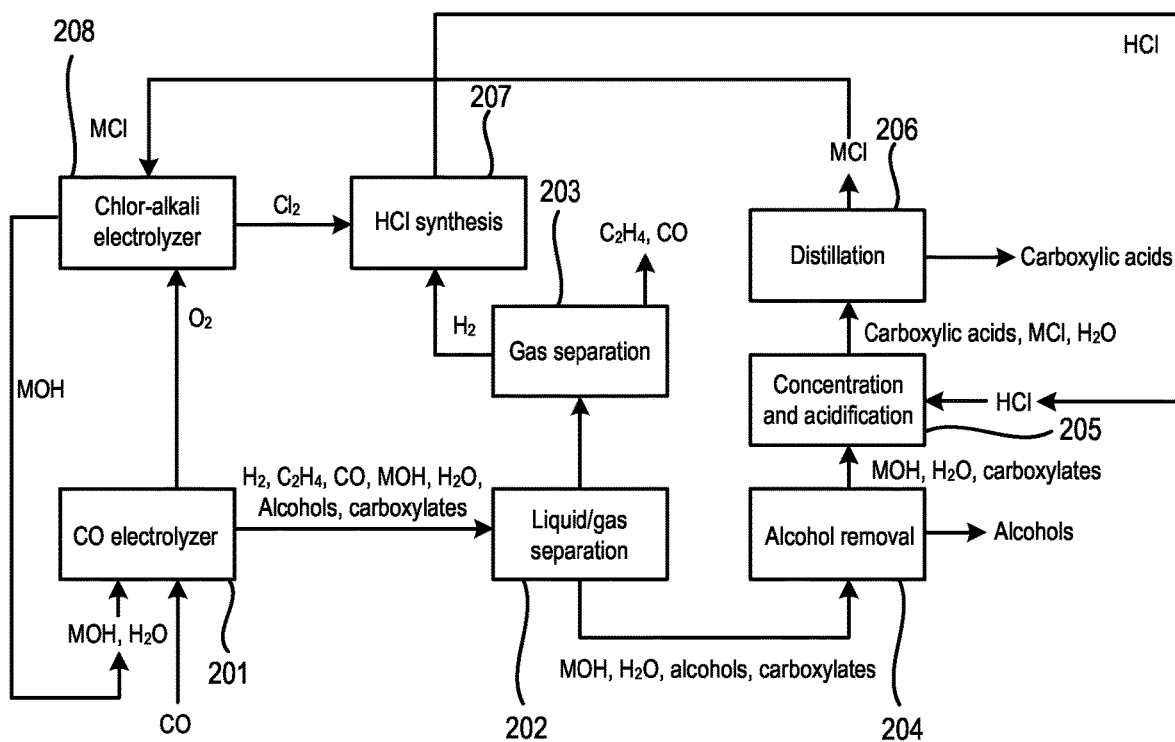
FIG. 2 illustrates integration of the CO electrolyzer process chain from FIG. 1 with a chlor-alkali electrolyzer in accordance with specific embodiments of the inventions disclosed herein.

FIG. 2 illustrates the integration of the CO electrolyzer process chain from FIG. 1 with a chlor-alkali electrolyzer 208. In specific embodiments of the invention, the chlor-alkali electrolyzer can be an oxygen-depolarized chlor-alkali membrane electrolyzer that produces chlorine gas and alkali metal hydroxide from an input of purified oxygen gas and a metal salt illustrated by metal chloride MCl in the FIG. 2. For example, the metal could be potassium or sodium. The chlorine gas from the chlor-alkali electrolyzer can be provisioned into an HCl synthesis reactor (e.g., a combustion chamber) together with dihydrogen from the CO electrolyzer 201 to produce HCl, and the alkali metal hydroxide can be provisioned into the CO electrolyzer 201 after purification to supply the alkaline equivalents required to operate the electrolyzer. Dioxygen is provisioned from the anode area of CO electrolyzer 201 and into the cathode area of the chlor-alkali electrolyzer 208. The CO electrolyzer product stream is subjected to a gas/liquid separation (e.g. gas/liquid separation unit 202), followed by acidification of the electrolyte and distillation of liquid products. The isolated aqueous phase, containing metal salt, is conditioned and recirculated back to the chlor-alkali electrolyzer 208 to produce the alkaline equivalents required to operate the CO electrolyzer 201. Heat from exothermic process subunits, such as but not limited to the HCl synthesis reactor 207 and/or combustion chamber, can be used to supply the heat required to operate separation subunits in the overall process chain.

The combination of an oxygen-depolarized chlor-alkali electrolyzer 208 and HCl synthesis reactor with a CO electrolyzer 201 is unique because there are benefits that cannot be easily realized by other forms of electrolyzers. The CO electrolyzer 201 can provide a high-purity source of dioxygen for the chlor-alkali electrolyzer 208 cathode, which minimizes upstream purification costs required to scrub and purify dioxygen for the chlor-alkali electrolyzer 208 cathode. Furthermore, alkaline CO electrolyzers (e.g., CO electrolyzers with alkaline electrolytes) are uniquely suited to take the alkali metal hydroxide and HCl produced by the combined chlor-alkali/HCl synthesis processes because electrolyzer processes typically do not consume stoichiometric amounts of base and acid. The chlor-alkali reactor can provide water to the CO electrolyzer or water can be provided from another source.

The provisioning of high-purity dioxygen to the chlor-alkali electrolyzer lowers the voltage and improves the purity of the chlor-alkali electrolyzer product stream. Because the kinetics of the oxygen depolarized cathode depend in great part on the concentration of the dioxygen provisioned to the cathode, it has been necessary for process operators to purify and concentrate dioxygen from air prior to feeding dioxygen into the oxygen depolarized cathode, using methods such as but not limited to absorption, pressure swing adsorption, membrane-based separation processes, and cryogenic separation. These upstream purification processes represent a cost to process operators.

The use of pure dioxygen streams from the CO electrolyzer 201 instead of an unpurified or unscrubbed air source is beneficial for the quality of the alkali product of the chlor-alkali electrolyzer. Air contains hundred-ppm quantities of $CO_2$, which reacts with the alkali metal hydroxide product to produce alkali metal carbonates. Directly provisioning an alkali metal hydroxide solution containing a large proportion of alkali metal carbonate is undesirable for the performance of the CO electrolyzer because alkali metal carbonate salts can foul the anode, membrane, and cathode compartments of the CO electrolyzer 201, in addition to reducing the electrochemical process efficiency.

The rate of chlor-alkali synthesis and/or CO electrolysis can be controlled to match the rate required to provision acid and base equivalents. In some instances, the CO electrolyzer 201 can produce little to no acetate, which reduces the feedstock acid and base equivalents required to operate the electrolyzer. CO electrolyzer 201 can be configured to produce little to no acetate by adjusting the operating conditions and/or the components of the CO electrolyzer 201. In some embodiments, the product stream from the CO electrolyzer can be largely composed of acetate, depending on how the electrolyzer is operated and configured, requiring a method to supply acid and base equivalents to valorize the acetate product.

In some embodiments of the invention, the degree of $H_2$ offtake from the CO electrolyzer 201 into the HCl synthesis reactor can be partial, depending on the amount of acetate produced in the electrolyzer. The downstream subunits of the CO electrolyzer 201 include a gas/liquid separation unit 202 to recover gaseous products from the output stream departing the electrolyzer, a gas separation unit 203 placed downstream of the gas/liquid separation unit, and an alcohol removal system 204 placed downstream of the liquid/gas separation subunit to recover alcohol products from the CO electrolyzer. The alcohol removal system can use methods such as but not limited to distillation, adsorption, or solvent based extraction to separate and recover the alcohol products. The downstream subunits further include a concentration and/or acidification subunit 205, downstream of the alcohol removal subunit, to convert the metal carboxylate products into carboxylic acid, co-producing a salt solution in water. The acidification subunit 205 takes as an input an acid HX, such as hydrochloric acid HCl, which is converted into a metal salt MCl through the acidification of the input carboxylates. A liquid product separation method such as but not limited to distillation 206 and/or solvent based extraction can be used to separate the carboxylic acid from the aqueous salt solution.

Figure 3:
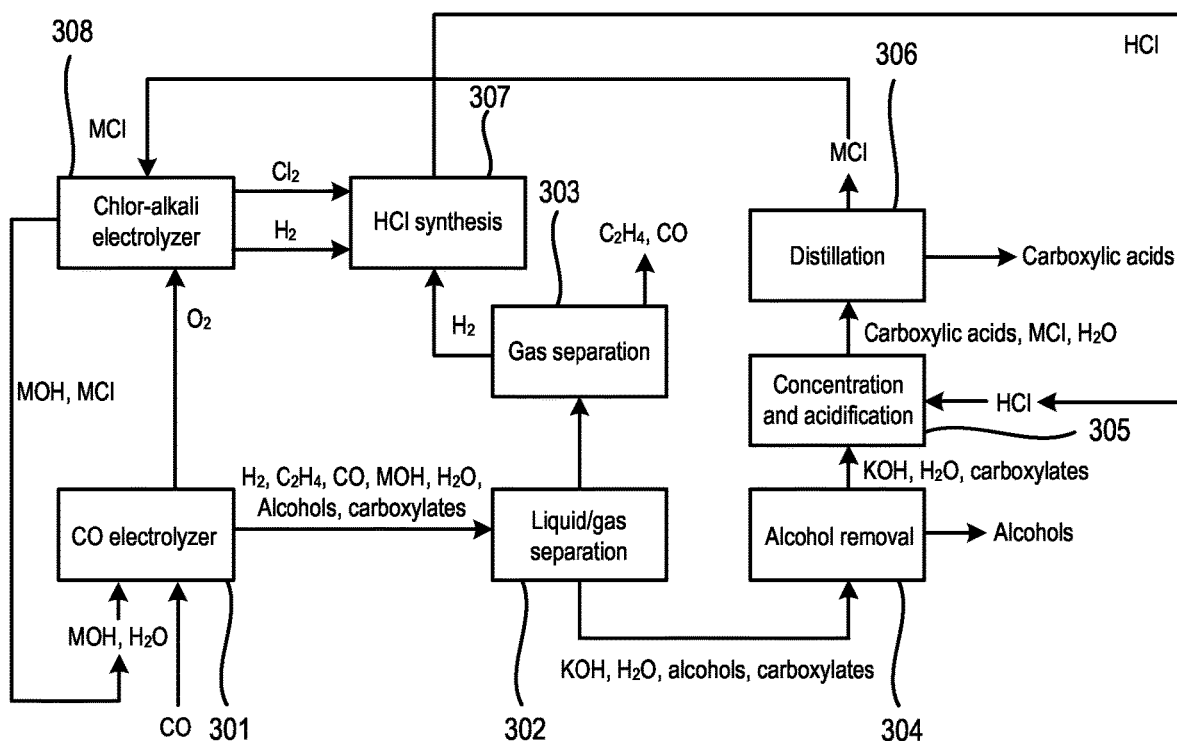
FIG. 3 illustrates the combination of a chlor-alkali electrolyzer and HCl synthesis system with a CO electrolyzer in accordance with specific embodiments of the inventions disclosed herein.

FIG. 3 illustrates that the chlor-alkali electrolyzer cathode can be operated partially depolarized, meaning that the cathode can both consume dioxygen provisioned from the CO electrolyzer 301 and simultaneously generate dihydrogen which is accompanied by the generation of hydroxide. The figure also shows how HCl can be generated by an HCl synthesis reactor 307 which receives chlorine gas from chlor-alkali electrolyzer 308 and CO electrolyzer 301 via gas separation unit 303. Chlor-alkali electrolyzers 308 can be operated such that the cathode evolves dihydrogen while the anode oxidizes chloride to chlorine gas. However, instead of evolving dihydrogen, oxygen can be provisioned into the cathode compartment to affect the oxygen reduction reaction and lower the voltage of the chlor-alkali electrolyzer 308. Depolarization of an electrolyzer cathode reduces the voltage of the system by providing an advantageously reducible substrate to the cathode. During such an operation mode, controls need to be taken to ensure that the dihydrogen and dioxygen within the chlor-alkali electrolyzer 308 remains below explosive limits.

In accordance with the disclosure above, the aforementioned operation mode can be utilized to modify the amount of hydrogen produced for acid synthesis against the amount of chlorine gas produced by the chlor-alkali electrolyzer. In cases in which the amount of dihydrogen generated in the CO electrolyzer 301 is in excess of the amount required to generate the HCl equivalents required to supply the acidification module, the dihydrogen can instead be stored for alternative use or can be fed to the chlor-alkali reactor to assist in the production of additional chlorine gas.

In another example, the method above is modified such that the chlor-alkali electrolyzer 308 is not depolarized with dioxygen and instead evolves dihydrogen. In this embodiment, dihydrogen from the chlor-alkali electrolyzer 308 is provisioned into the HCl combustion chamber along with chlorine gas to produce HCl required to protonate alkali metal carboxylates produced by the CO electrolyzer 301. Alternatively, if the amount of acid equivalents required is low, such as but not limited to embodiments wherein the CO electrolyzer 301 produces a low amount of metal carboxylate, the dihydrogen can instead be provisioned into the anode area of the CO electrolyzer 301 to lower the overall process energy consumption of the CO electrolyzer 301.

The provisioning of the dihydrogen generated by a chlor-alkali electrolyzer 308 into the acid synthesis module servicing the CO electrolyzer product stream or into the product stream itself provides for a way for the dihydrogen generated by the chlor-alkali electrolyzer 308 to be effectively valorized. In many cases, it has not been economically feasible for chlor-alkali process operators to isolate the dihydrogen produced by the chlor-alkali electrolyzer 308, because of the downstream processing requirements that are necessary to valorize the dihydrogen produced. In some cases, the dihydrogen can be valorized as a feedstock for other processes such as but not limited to ammonia, hydrogen peroxide, methanol, and hydrochloric acid synthesis. In some cases dihydrogen is flared to heat steam or produce heat, which is a relatively inefficient use of electrolytically generated dihydrogen. It has not been obvious for the dihydrogen from a chlor-alkali electrolyzer 308 to be integrated into an acid synthesis and acidification module because other electrolyzer types beyond the CO electrolyzer 301 do not typically produce an alkaline product stream that requires acidification to be effectively valorized as a commercial product.

The downstream subunits include a liquid/gas separation unit 302 to recover gaseous products from the output stream departing the electrolyzer, a gas separation unit 303 placed downstream of the gas/liquid separation unit, and an alcohol removal system 304 placed downstream of the liquid/gas separation subunit to recover alcohol products from the CO electrolyzer. The alcohol removal system can use methods such as but not limited to distillation, adsorption, or solvent based extraction to separate and recover the alcohol products. The downstream subunits further include a concentration and/or acidification subunit 305, downstream of the alcohol removal subunit, to convert the metal carboxylate products into carboxylic acid, co-producing a salt solution in water. The acidification subunit takes as an input an acid HX, such as hydrochloric acid HCl, which is converted into a metal salt MX through the acidification of the input carboxylates. A liquid product separation method such as but not limited to distillation 306 and/or solvent based extraction can be used to separate the carboxylic acid from the aqueous salt solution.

Figure 4:
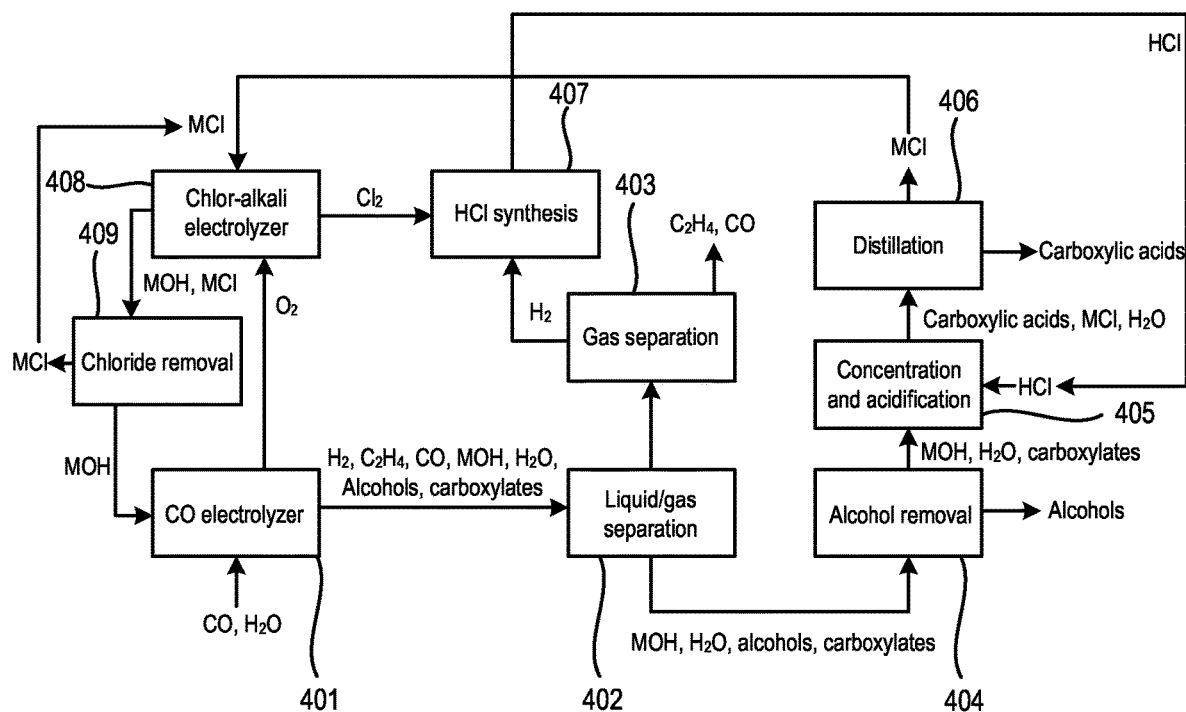
FIG. 4 illustrates the combination of a chlor-alkali electrolyzer and a CO electrolyzer in which a chloride removal system prevents chloride from being provided to the CO electrolyzer in accordance with specific embodiments of the inventions disclosed herein.

In another example, the method above is modified as illustrated in FIG. 4 such that the chlor-alkali electrolyzer 408 is a diaphragm cell that produces an alkali metal hydroxide stream containing chloride ions and hypochlorite ions. In such an embodiment, undesired anions such as but not limited to chloride and hypochlorite are removed from the chlor-alkali liquid product stream in order to condition the electrolyte to be suitable for use in the CO electrolyzer 401. These ions must be separated from the hydroxide prior to provision into the CO electrolyzer 401 using a method such as but not limited to nanofiltration, reverse osmosis, precipitation, chemical precipitation using barium salts, electrodialysis, diffusion dialysis, salt removal using liquid ammonia, and ion adsorption to remove the chloride from the liquid stream. Anions such as chloride are undesirable for intrusion into the CO electrolyzer 401 because parts of the CO electrolyzer 401 can foul in response to the presence of chloride. For example, stainless steel, nickel, and iridium-based parts (e.g., valves, pumps, compressors, fittings, heaters, thermocouples, bipolar plates, stack housing, electrode supports) and electrodes can corrode over time when exposed to chloride, limiting the effective lifetime of the electrolyzer system.

The downstream subunits include a liquid/gas separation unit 402 to recover gaseous products from the output stream departing the electrolyzer, a gas separation unit 403 placed downstream of the gas/liquid separation unit, and an alcohol removal system 404 placed downstream of the liquid/gas separation subunit to recover alcohol products from the CO electrolyzer. The alcohol removal system can use methods such as but not limited to distillation, adsorption, or solvent based extraction to separate and recover the alcohol products. The downstream subunits further include a concentration and/or acidification subunit 405, downstream of the alcohol removal subunit, to convert the metal carboxylate products into carboxylic acid, co-producing a salt solution in water. The acidification subunit takes as an input an acid HX, such as hydrochloric acid HCl, which is converted into a metal salt MX through the acidification of the input carboxylates. A liquid product separation method such as but not limited to distillation 406 and/or solvent based extraction can be used to separate the carboxylic acid from the aqueous salt solution. Further, HCl synthesis is performed in HCl synthesis reactor 407. Downstream of the chlor-alkali electrolyzer chloride removal is performed by a chloride removal unit 409.

Figure 5:
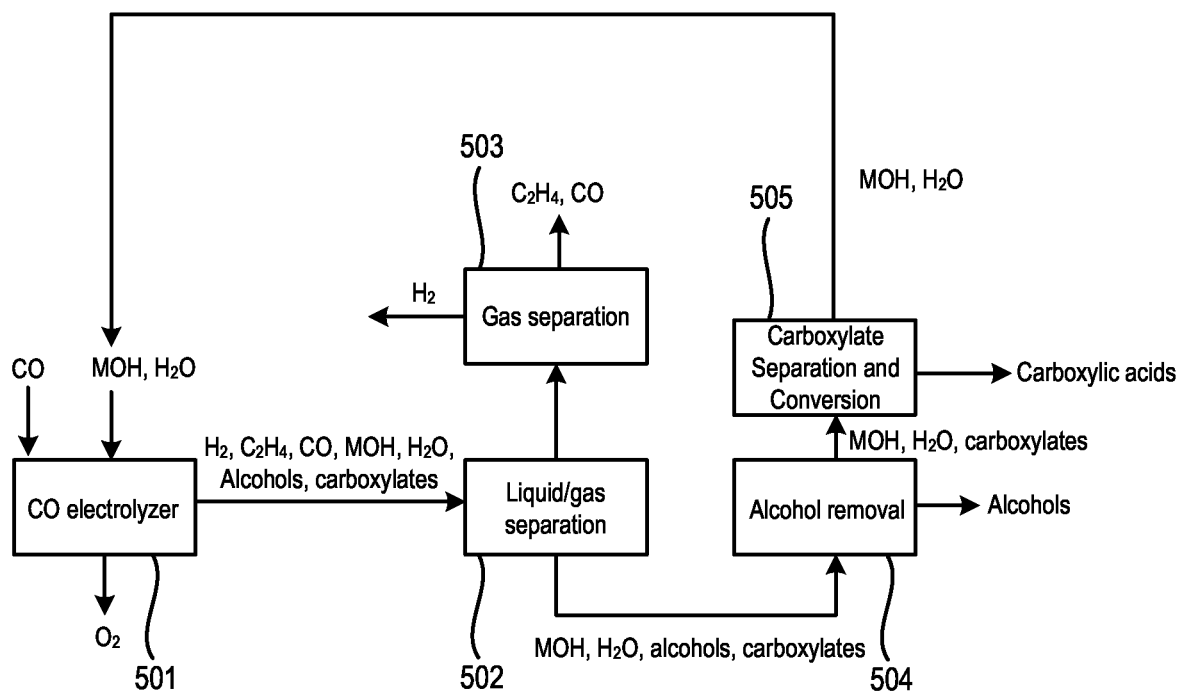
FIG. 5 illustrates a process chain in which direct acidification is not employed to recover carboxylic acids from a CO electrolyzer outlet stream to minimize the amount of acid and base equivalents used in the process chain in accordance with specific embodiments of the inventions disclosed herein.

In some embodiments of the invention, the method above is modified as illustrated in FIG. 5 such that direct acidification is not employed to recover carboxylic acids from the CO electrolyzer 501 outlet stream to minimize the amount of acid and base equivalents used in the process chain. The carboxylic acid or carboxylate recovery process can instead use another method to separate alkali metal carboxylate and alkali metal hydroxide, such as but not limited to precipitation, solvent based extraction, electrodialysis, and others. As such, in any embodiment disclosed herein in which hydrochloric acid is produced in the system, the hydrochloric acid does not necessarily need to be consumed to help to form carboxylic acid and/or recycle a metal salt and can instead be used for other purposes.

In another example, the method above is modified to include a reactive extraction process to maximize the recovery of carboxylates from the CO electrolyzer 501 output before the stream is acidified and minimize the amount of alkaline equivalents acidified. Examples include but are not limited to esterification and use of the carboxylate as a nucleophile for an electrophile partner in an organic phase.

In another example, the method above is modified to include hydrogen peroxide and alkali metal oxides such as but not limited to $Na_2O$ and $K_2O$ produced in the chlor-alkali electrolyzer to be mixed with water and provisioned to the anode area of the CO electrolyzer 501, lowering the voltage of the overall process.

In another example, the method above is modified such that alkali metal hydroxide is incompletely converted to alkali metal carboxylate within the CO electrolyzer 501, producing an electrolyte stream partially composed of alkali metal hydroxide. Uptake of this stream into a downstream acidification module incurs waste because the hydroxide is reacted with acid. To supply the electrolyzer with sufficient alkali metal hydroxide for efficient operation, alkali metal hydroxide must be supplied externally. The downstream subunits include a liquid/gas separation unit 502 to recover gaseous products from the output stream departing the electrolyzer, a gas separation unit 503 placed downstream of the gas/liquid separation unit, and an alcohol removal system 504 placed downstream of the liquid/gas separation subunit to recover alcohol products from the CO electrolyzer. The alcohol removal system can use methods such as but not limited to distillation, adsorption, or solvent based extraction to separate and recover the alcohol products. The downstream subunits further include a reactive extraction of carboxylate subunit 505, downstream of the alcohol removal subunit, to convert the metal carboxylate products into carboxylic acid, co-producing an alkali solution in water.

The downstream subunits include a liquid/gas separation unit 502 to recover gaseous products from the output stream departing the electrolyzer, a gas separation unit 503 placed downstream of the gas/liquid separation unit, and an alcohol removal system 504 placed downstream of the liquid/gas separation subunit to recover alcohol products from the CO electrolyzer. The downstream subunits further include a metal carboxylate and metal hydroxide separation and reactive extraction of carboxylate subunit 505 such as a carboxylate to carboxylic acid conversion unit, downstream of the alcohol removal subunit, to convert the metal carboxylate products into carboxylic acid, MOH in water. The MOH and water is passed to the CO electrolyzer 501.

Figure 6:
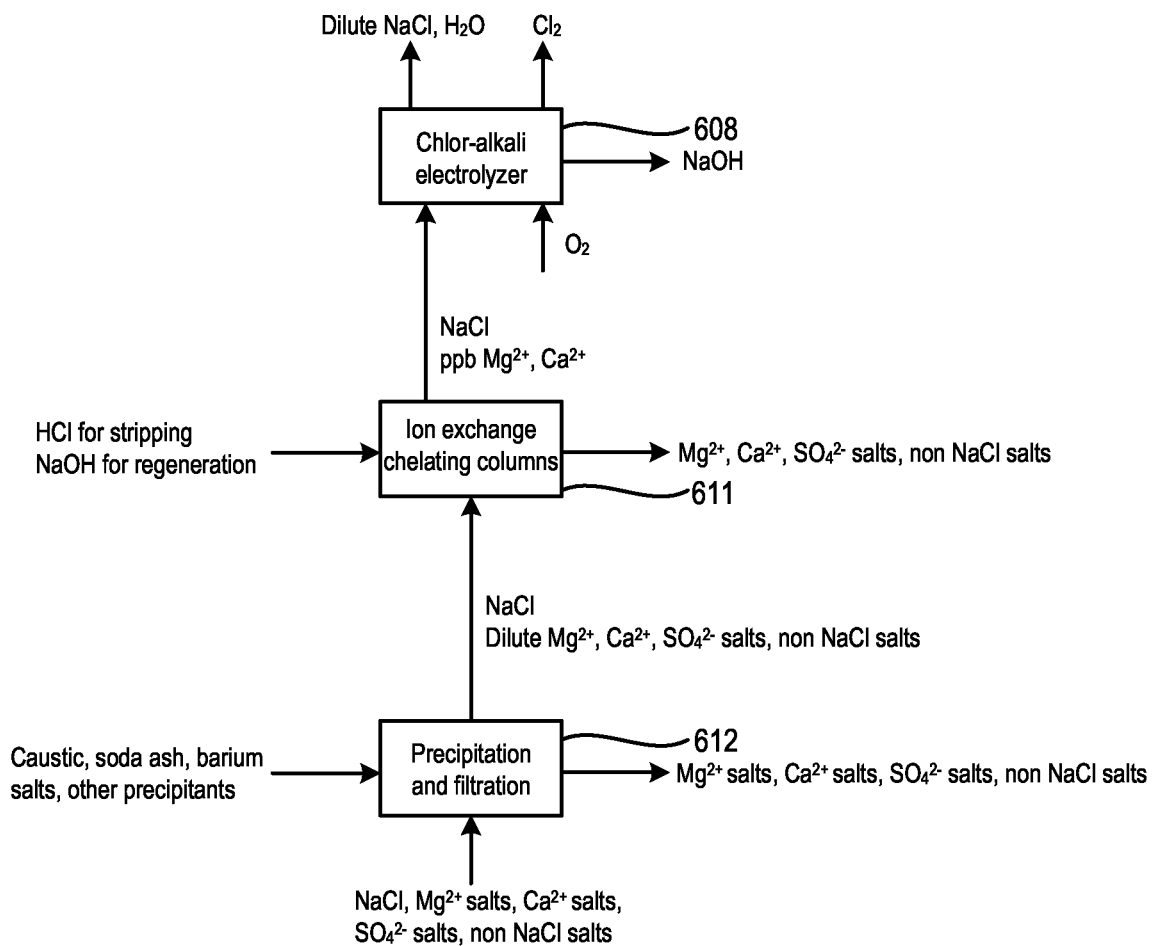
FIG. 6 illustrates an upstream purification process required to remove divalent ions in the brine feed to the chlor-alkali electrolyzer in accordance with specific embodiments of the inventions disclosed herein.

In another example, the method above is modified as illustrated in FIG. 6 such that an upstream purification process required to remove divalent ions in the brine feed to the chlor-alkali electrolyzer 608 is obviated by the use of purified brine from the CO electrolyzer. This specific integration scheme leads to energy savings because the necessity of removing divalent ions from the brine stream prior to entering the chlor-alkali electrolyzer 608 imposes an energy demand and loss of system productivity because it is necessary to consume equivalents of acid (to regenerate ion exchange or chelating columns 611) and/or base (to precipitate the multivalent cations). As a nonlimiting example, it can be necessary to remove $Mg^{2+}$ from a chlor-alkali brine feed such that the $Mg^{2+}$ concentration is at the ppm level. In many cases, $Mg^{2+}$ is removed by precipitating it as a solid such as but not limited to $Mg(OH)_2$ via its reaction with electrogenerated OH", which means that every equivalent of $Mg^{2+}$ present in the brine feed consumes two equivalents of the desired alkali metal hydroxide product in the electrolyzer. A precipitation and filtration subunit 612 transfers salts to the ion exchange or chelating columns 611.

Figure 7:
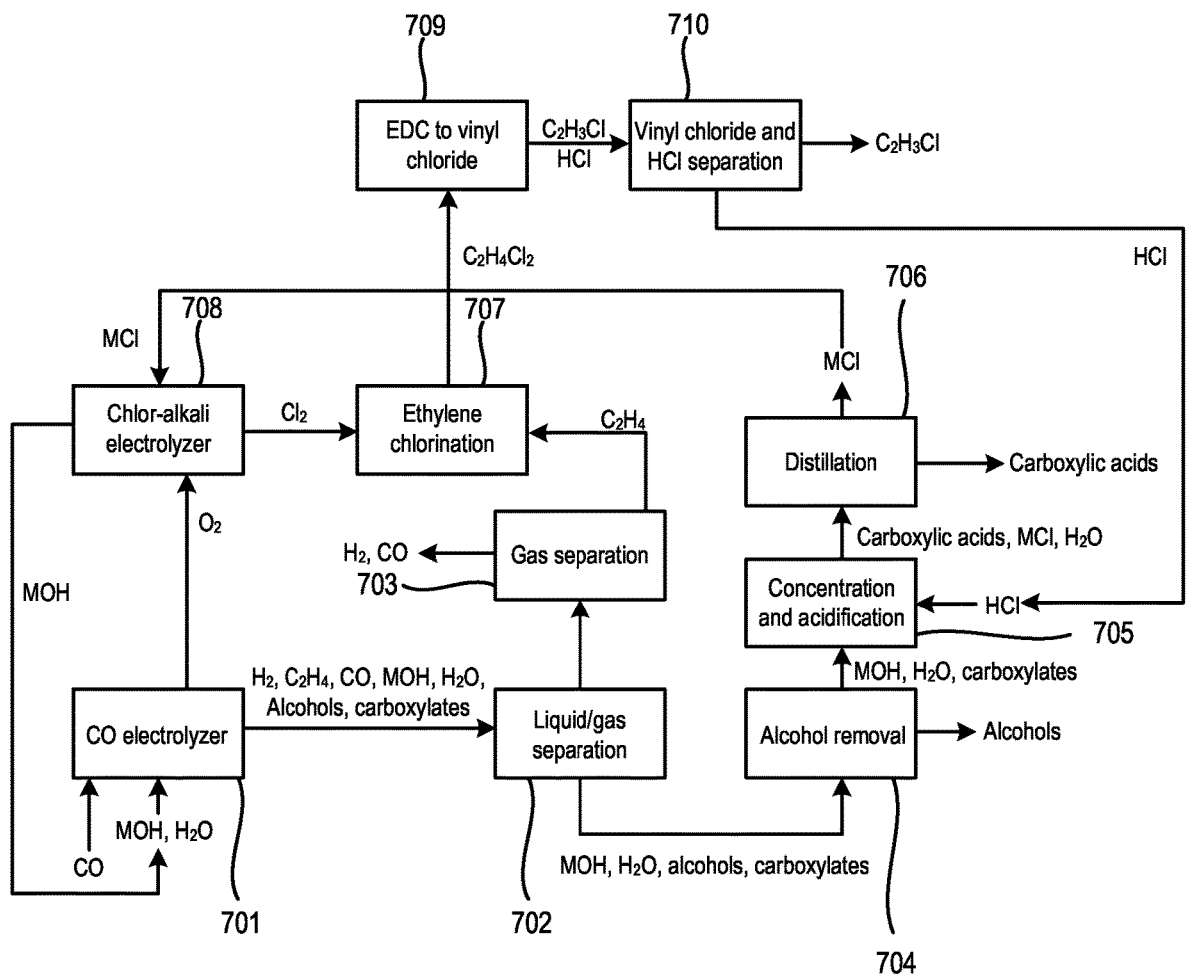
FIG. 7 illustrates a chlor-alkali electrolyzer and a CO electrolyzer integrated with a vinyl chloride production system using an ethylene chlorination reactor in accordance with specific embodiments of the inventions disclosed herein.

In another example, the method above is modified as illustrated in FIG. 7 such that a chlor-alkali electrolyzer 708 and a CO electrolyzer 701 are integrated with a vinyl chloride production system that produces fewer emissions compared to a fully fossil-based system. In such a process, ethylene and chlorine gas are provisioned from the CO electrolyzer 701 and chlor-alkali electrolyzers 708, respectively, into the ethylene chlorination subunit. The CO electrolyzer product stream including ethylene and/or dioxygen are provisioned into an ethylene chlorination and chlor-alkali electrolyzer, respectively. It is advantageous for vinyl chloride production systems to integrate a CO electrolyzer 701 because the high purity of ethylene produced by a CO electrolyzer 701 obviates the use of purification systems required to condition the feedstock of a vinyl chloride production plant, which typically requires the separation of compounds such as propene and propane to minimize the formation of chloropropanes and chloropropenes, which are challenging to separate from the ethylene dichloride intermediate. Additionally, it is advantageous for vinyl chloride production systems to integrate a CO electrolyzer 701 because it provides a mechanism to lower the direct greenhouse gas emissions of the vinyl chloride process incurred by the reforming, combustion, and/or partial oxidation of ethylene during the synthesis of ethylene dichloride. Another benefit of integrating the vinyl chloride synthesis process chain with a CO electrolyzer 701 is the opportunity to valorize the HCl byproduct generated by the conversion of ethylene dichloride to vinyl chloride, which is generally treated as waste but can be advantageously used by either the chlor-alkali process in brine pretreatment or by the CO electrolyzer 701 process chain for product acidification.

The downstream subunits include a liquid/gas separation unit 702 to recover gaseous products from the output stream departing the electrolyzer, a gas separation unit 703 placed downstream of the gas/liquid separation unit, and an alcohol removal system 704 placed downstream of the liquid/gas separation subunit to recover alcohol products from the CO electrolyzer. The downstream subunits also include, downstream of the alcohol removal subunit, a concentration and acidification subunit 705 to convert the metal carboxylate products into carboxylic acid, MOH in water. The acidification subunit takes as an input an acid HX, such as hydrochloric acid HCl, which is converted into a metal salt MX through the acidification of the input carboxylates. A liquid product separation method such as but not limited to distillation 706 and/or solvent based extraction can be used to separate the carboxylic acid from the aqueous salt solution. Ethylene chloride from the ethylene chlorination subunit 707 is passed to EDC or vinyl chloride subunit 709. Vinyl chloride is obtained from vinyl chloride and HCl separation unit 710.

Figure 8:
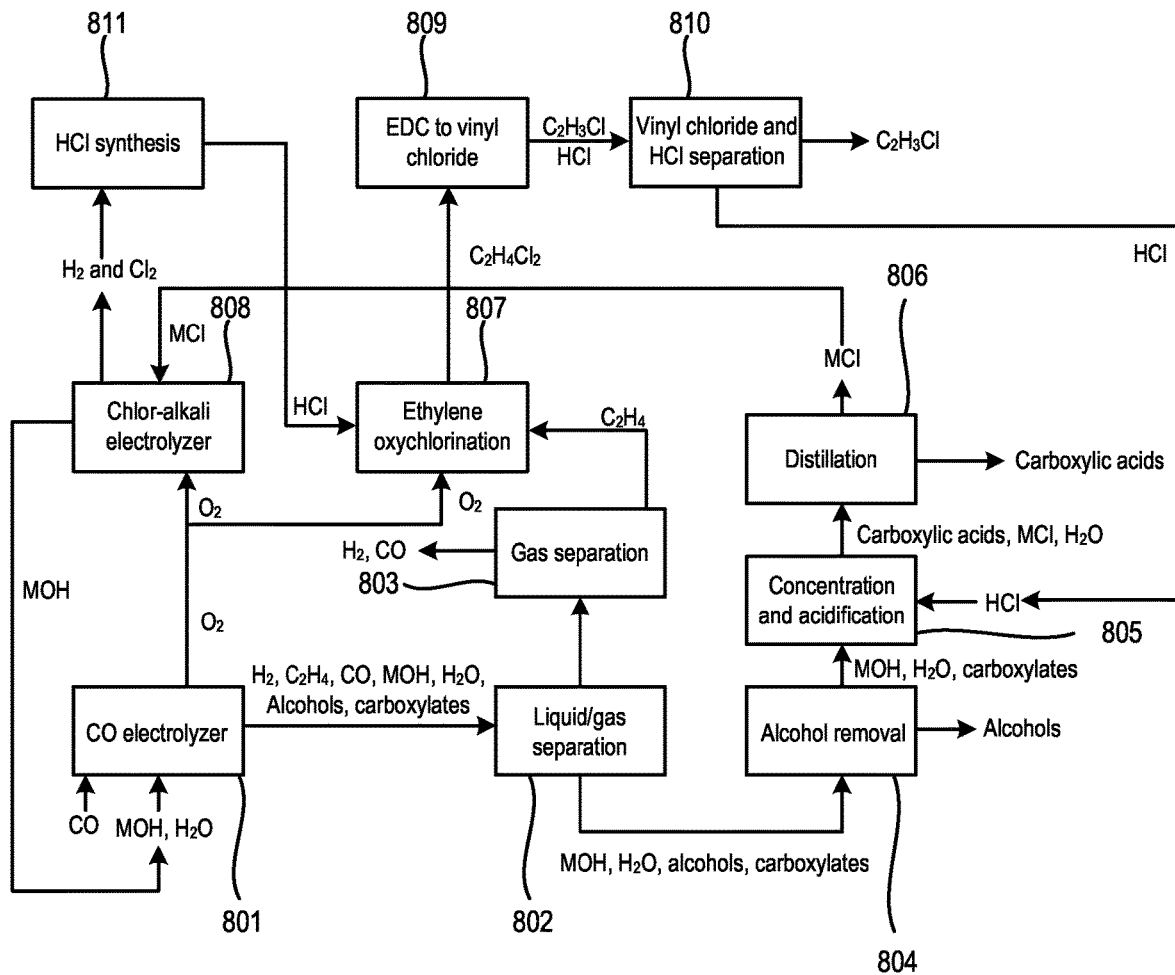
FIG. 8 illustrates a chlor-alkali electrolyzer and a CO electrolyzer integrated with a vinyl chloride production system using ethylene oxychlorination in accordance with specific embodiments of the inventions disclosed herein.

In specific embodiments, the method above is modified as illustrated in FIG. 8 such that the ethylene chlorination process uses dioxygen from the CO electrolyzer 801 to lower the energy demand of the process. In such a process, an ethylene oxychlorination subunit 807 is provided dioxygen and ethylene from the CO electrolyzer 801, and HCl from another source. In the illustrated case the other source for the HCl can be generated from the combination of dihydrogen and chlorine gas in an HCl synthesis reactor where the chlorine is from the chlor-alkali electrolyzer 808 and the dihydrogen is from either the chlor-alkali electrolyzer 808 as illustrated or from the CO electrolyzer. The efficiency of an ethylene oxychlorination subunit 807 is improved by the use of dioxygen instead of air as a feedstock. The use of dioxygen instead of air also improves the ethylene utilization of the ethylene dichloride synthesis process. Operators of an ethylene oxychlorination plant incur an energy, capital, and operational cost to purify dioxygen out of air using methods such as but not limited to membrane-based separation processes, pressure and temperature swing adsorption processes, and cryogenic separation. Sourcing dioxygen from the CO electrolyzer is advantageous because it is of high purity and provides a route to valorize the dioxygen produced by the CO electrolyzer, leading to synergy between the two processes. HCl to supply the ethylene oxychlorination process can be sourced from a number of sources elsewhere in the process chain, such as but not limited to the HCl byproduct from vinyl chloride synthesis, HCl combustion from the combination of $H_2$ and $Cl_2$, and/or a downstream chemical process producing excess HCl such as but not limited to the incineration of polyvinylchloride or the production of dichloromethane and other organochlorine compounds.

The downstream subunits include a liquid/gas separation unit 802 to recover gaseous products from the output stream departing the electrolyzer, a gas separation unit 803 placed downstream of the gas/liquid separation unit, and an alcohol removal system 804 placed downstream of the liquid/gas separation subunit to recover alcohol products from the CO electrolyzer. Downstream of the alcohol removal subunit, concentration and acidification unit 805 converts the carboxylate products into carboxylic acid. The acidification subunit takes as an input an acid HX, such as hydrochloric acid HCl, which is converted into a metal salt MX, such as MCL, through the acidification of the input carboxylates. A liquid product separation method such as but not limited to distillation 806 and/or solvent based extraction can be used to separate the carboxylic acid from the aqueous salt solution. MOH from the Chlor-alkali electrolyzer 808 is passed to the CO electrolyzer 801. Further, EDC to vinyl chloride subunit 809 converts ethylene dichloride to vinyl chloride. Vinyl chloride and HCl is obtained from vinyl chloride and HCl separation unit 810. HCl synthesis is performed in the HCl synthesis subunit 811 and the HCl produced is passed to the ethylene oxychlorination subunit 807.

Figure 9:
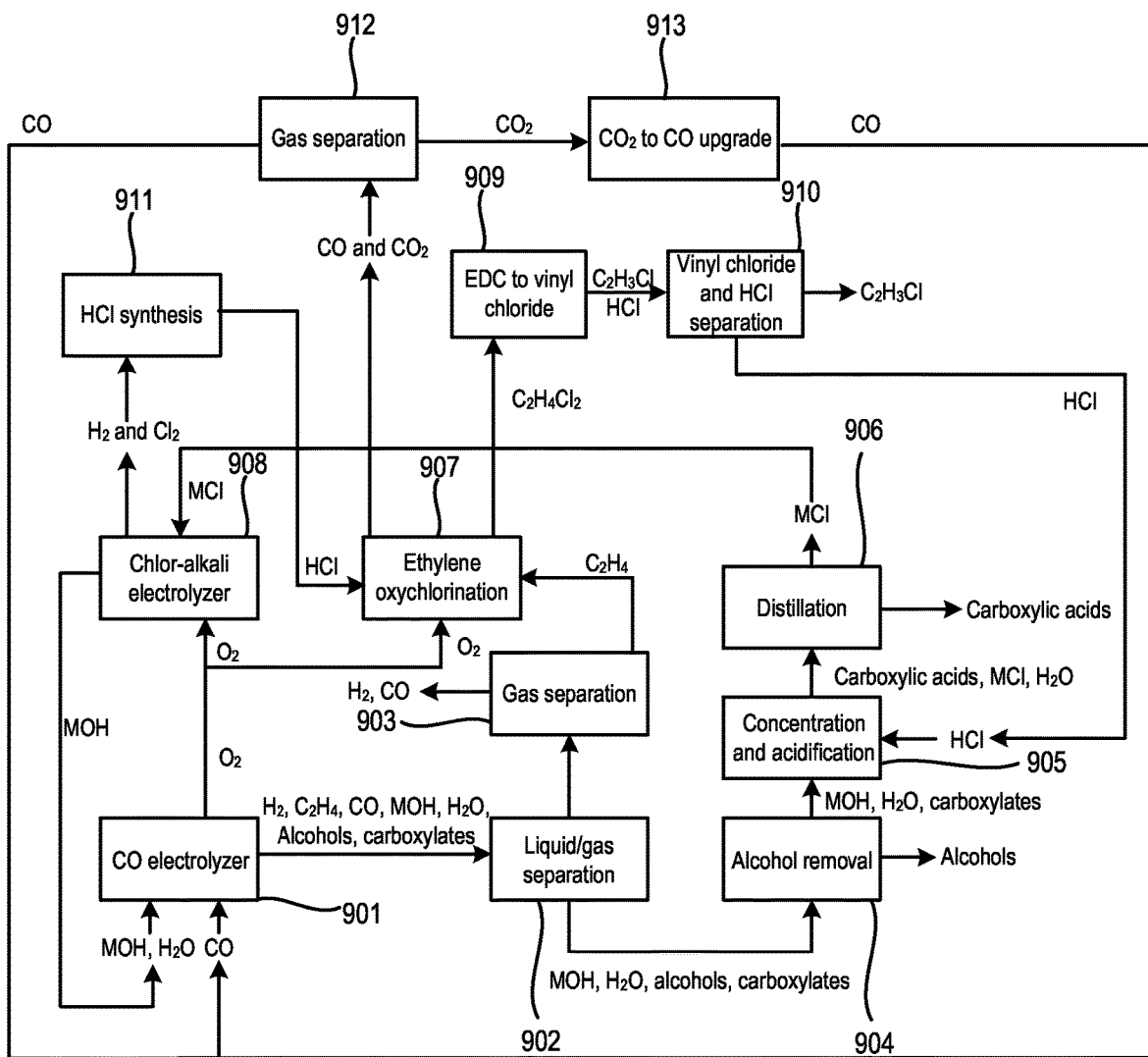
FIG. 9 illustrates a gas separation and purification system downstream of the ethylene oxychlorination process of FIG. 8 which harvests the CO and $CO_2$ generated thereby for use in the CO electrolyzer and upgrading into CO, respectively, in accordance with specific embodiments of the inventions disclosed herein.

FIG. 9 illustrates a modification to the systems above such that a gas separation and purification system is implemented downstream of the ethylene oxychlorination process which harvests the CO and $CO_2$ generated by ethylene oxychlorination unit 907 for use in the CO electrolyzer 901 and upgrading into CO, respectively. In this embodiment, the greenhouse gas emissions intensity of the overall process can be mitigated by converting the carbon oxides emitted by the ethylene oxychlorination unit into ethylene and other value-added chemicals. The $CO_2$ can be valorized via thermochemical, electrochemical, or plasma-based processes such as but not limited to solid-oxide electrolysis, RWGS, direct $CO_2$ hydrogenation, or low-temperature $CO_2$ electrolysis. The reducing equivalents required to convert the $CO_2$ to CO can be sourced from elsewhere in the process chain, such as but not limited to the dihydrogen generated by the chlor-alkali electrolyzer 908 and CO electrolyzer 901 or a separate water electrolyzer. Prior to provision into the CO electrolyzer 901, $CO_2$ and other impurity gases such as but not limited to HCl and $Cl_2$ are separated and conditioned from the effluent gas stream for efficient operation of the CO electrolyzer 901.

The downstream subunits include a liquid/gas separation unit 902 to recover gaseous products from the output stream departing the electrolyzer, a gas separation unit 903 placed downstream of the gas/liquid separation unit, and an alcohol removal system 904 placed downstream of the liquid/gas separation subunit to recover alcohol products from the CO electrolyzer. Downstream of the alcohol removal subunit, a concentration and acidification unit 905 converts the metal carboxylate products into carboxylic acid. The acidification subunit takes as an input an acid HX, such as hydrochloric acid HCl, which is converted into a metal salt MX, such as MCL, through the acidification of the input carboxylates. A liquid product separation method such as but not limited to distillation 906 and/or solvent based extraction can be used to separate the carboxylic acid from the aqueous salt solution. MOH from the chlor-alkali electrolyzer 908 is passed to the CO electrolyzer 901. Further, EDC to vinyl chloride subunit 909 converts ethylene dichloride to vinyl chloride. Vinyl chloride is obtained from vinyl chloride and HCl separation unit 910. HCl synthesis is performed in the HCl synthesis subunit 911 and the HCl is produced is passed to the ethylene oxychlorination unit 907. CO generated from the CO electrolyzer 901 is transferred to a gas separation unit 912 to produce $CO_2$. Further, $CO_2$ is converted to CO in a $CO_2$ to CO upgrade unit 913.

Figure 10:
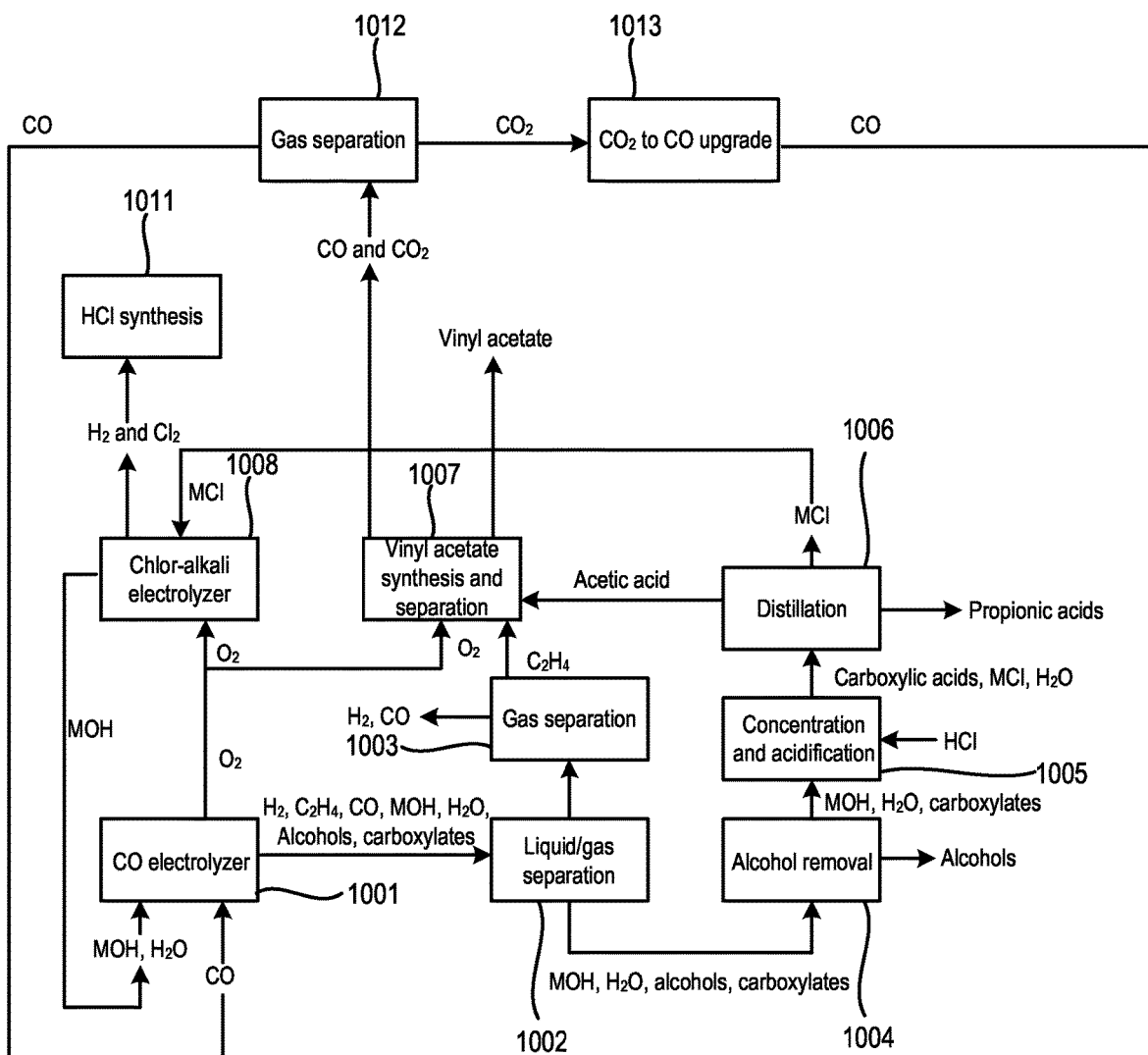
FIG. 10 illustrates chlor-alkali and CO electrolyzers integrated into a process that includes a vinyl acetate synthesis and separation system that lowers the greenhouse gas emissions footprint of the vinyl acetate process chain in accordance with specific embodiments of the inventions disclosed herein.

In specific embodiments of the invention, as illustrated in FIG. 10, the chlor-alkali electrolyzer 1008 and CO electrolyzers 1001 are integrated into a broader process that includes a vinyl acetate synthesis and separation system 1007 that lowers the greenhouse gas emissions footprint of the vinyl acetate process chain. Vinyl acetate is industrially produced by the reaction of ethylene, acetic acid, and dioxygen, which are all products of the CO electrolyzer 1001, at elevated temperature via equation 1. Side-products of the vinyl acetate process from hydrocarbon reforming with byproduct water and the partial combustion of the ethylene and acetic acid inputs include CO and $CO_2$, via equations 2-6. The direct emissions of CO and $CO_2$ from the vinyl acetate process chain represents a liability to the process operators, but the integration of a $CO_2$ to CO upgrade unit 1013 and CO electrolyzer 1001 provides a mechanism by which operators can mitigate the cost of managing the direct emissions of vinyl acetate synthesis.

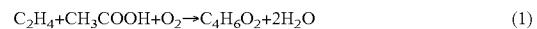

$$C_2H_4+CH_3COOH+O_2 \rightarrow C_4H_6O_2+2H_2O \quad (1)$$

$$C_2H_4+3O_2 \rightarrow 2CO_2+2H_2O \quad (2)$$

$$C_2H_4+2O_2 \rightarrow 2CO+2H_2O \quad (3)$$

$$C_2H_4+H_2O \rightarrow 2CO+3H_2 \quad (4)$$

$$C_2H_4+4H_2O \rightarrow 2CO_2+6H_2 \quad (5)$$

$$CH_3COOH+3O_2 \rightarrow 2CO_2+2H_2O \quad (6)$$

In addition to reducing the greenhouse gas emissions intensity of vinyl acetate synthesis, it is advantageous for a vinyl acetate synthesis process operator to integrate a CO electrolyzer 1001 into the process chain because the CO electrolyzer 1001 provides a source of pure ethylene, acetic acid, and dioxygen, reducing the purification costs required to supply the vinyl acetate synthesis system. For example, dioxygen must typically be sourced from air using energy and cost-intensive separation methods, adding cost to the production of vinyl acetate. The CO electrolyzer benefits from integration with the vinyl acetate process chain because it provides a route to valorize the dioxygen product of the CO electrolyzer 1001, provides a concentrated source of $CO_2$ to supply a $CO_2$ to CO upgrade unit to generate the CO feedstock required, and provides an offtake route for alkali metal carboxylates produced by the CO electrolyzer 1001, reducing the acidification demand of the CO electrolyzer system. Specifically, a vinyl acetate synthesis process requires the continual provision of alkali metal carboxylate as a reaction promoter. This is advantageous for the CO electrolyzer process chain because the requirement of acidifying the alkali metal carboxylate produced by the CO electrolyzer represents a cost in the form of the acid added and the alkali metal hydroxide neutralized by the added acid. In specific embodiments of the invention, carboxylate can be removed from the output stream without acidifying the output stream using electrodialysis or other methods. However, acidification is a beneficial approach in some instances. The downstream subunits include a vinyl acetate synthesis and separation system 1007 to recover vinyl acetate from the output stream departing the CO electrolyzer, a gas separation unit 1003 placed downstream of the gas/liquid separation unit 1002, and an alcohol removal system 1004 placed downstream of the liquid/gas separation subunit to recover alcohol products from the CO electrolyzer. The downstream of the alcohol removal subunit, concentration and acidification 1005 to convert the metal carboxylate products into carboxylic acid. The acidification subunit takes as an input an acid HX, such as hydrochloric acid HCl, which is converted into a metal salt MX, such as MCl, through the acidification of the input carboxylates. A liquid product separation method such as but not limited to distillation 1006 and/or solvent based extraction can be used to separate the carboxylic acid from the aqueous salt solution. MOH from chlor-alkali electrolyzer 1008 is passed to the CO electrolyzer 1001. CO generated from CO electrolyzer 901 is transferred to a gas separation unit 1012 to produce $CO_2$. Chlor-alkali electrolyzer 1008 produces dihydrogen and chlorine gas. The dihydrogen and chlorine gas formed are passed to HCl synthesis subunit 1011 to produce HCl.

Figure 11:
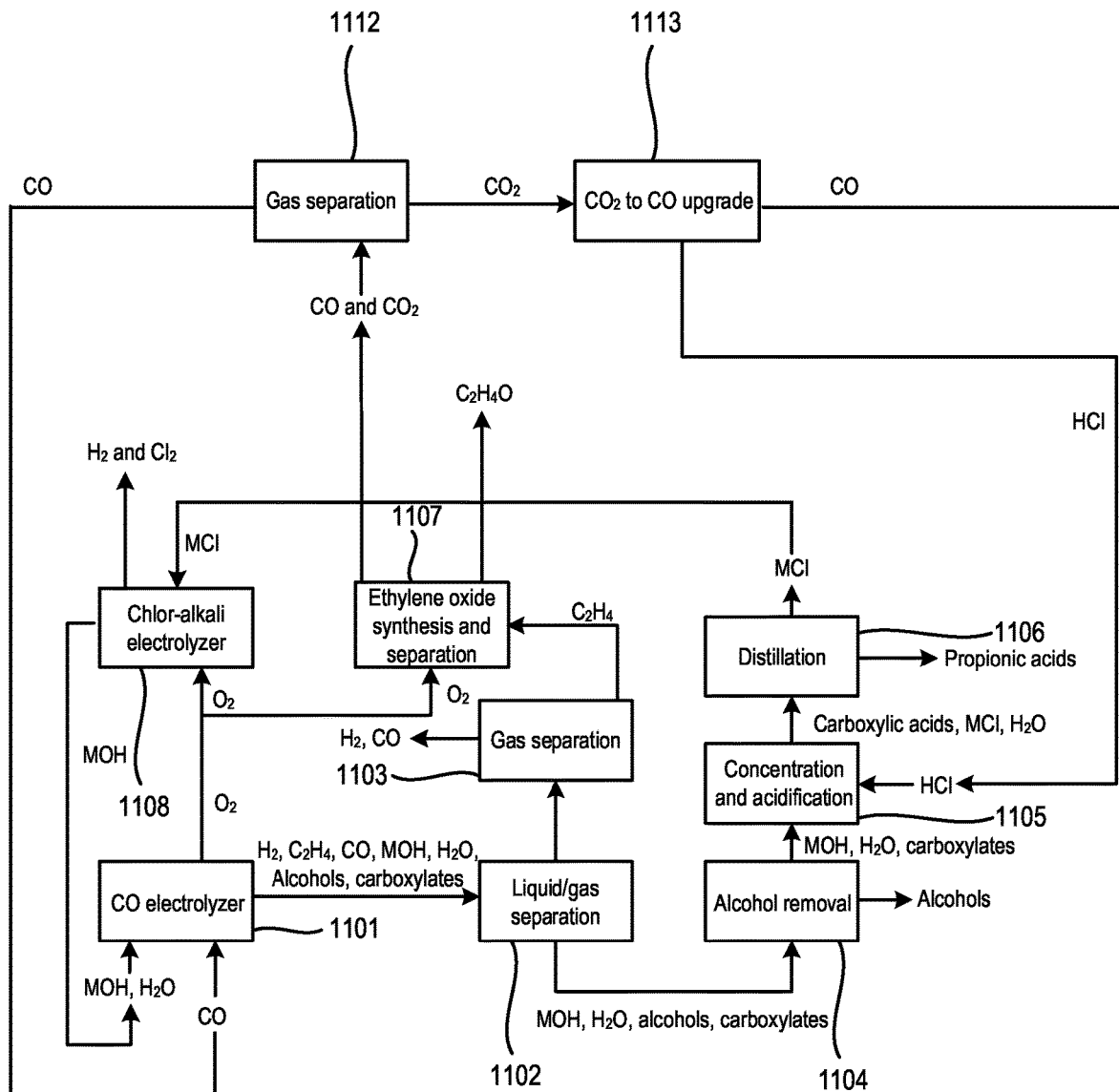
FIG. 11 illustrates an ethylene oxide production system integrated with a $CO_2$ to CO upgrade system to reduce the emissions footprint of the ethylene oxide production process in accordance with specific embodiments of the inventions disclosed herein.

In specific embodiments of the invention, methods above are modified as illustrated in FIG. 11 such that an ethylene oxide production system is integrated with the combination of a chlor-alkali electrolyzer 1108 and CO electrolyzer 1101 and a $CO_2$ to CO upgrade system 1113 to reduce the emissions footprint of the ethylene oxide production process. Ethylene oxide is produced by the oxidation of ethylene with dioxygen at elevated temperatures using a silver-based catalyst on a support, via equation 7. Side-products of this reaction include the oxidation of ethylene to CO and $CO_2$, in addition to reforming reactions with byproduct water as in equations 2-6 above.

$$C_2H_4 + \tfrac{1}{2}O_2 \rightarrow C_2H_4O \qquad (7)$$

In addition to reducing the greenhouse gas emissions intensity of ethylene oxide synthesis, it is advantageous for an ethylene oxide production system to integrate a CO electrolyzer 1101 because the CO electrolysis provides a high-purity source of both ethylene and dioxygen. The CO electrolyzer 1101 benefits from integration with the ethylene oxide process chain because it provides a route to valorize the dioxygen product of the CO electrolyzer 1101 and provides a concentrated source of $CO_2$ to supply a $CO_2$ to CO upgrade unit to generate the CO feedstock required.

In the specific embodiments detailed here, the degree of dioxygen offtake from the CO electrolyzer 1101 by any particular process subunit can be controlled by adjusting the flow of dioxygen from the CO electrolyzer 1101 to individual process subunits, depending on where maximal process benefits are attained by the provision of the dioxygen. In some embodiments, the chlor-alkali electrolyzer 1108 may be operated without an oxygen depolarized cathode and the dioxygen from the CO electrolyzer 1101 is instead provided to the vinyl acetate, vinyl chloride, and/or ethylene oxide process chains.

The energy required to power the electrochemical processes occurring at the cathode and anode of CO electrolyzer 1101 is minimized when a CO electrolyzer is operated with highly alkaline electrolyte, notably at the anode. Operating at high pH also enables the use of efficient, abundant metallic catalysts for the water oxidation reaction at the anode of the CO electrolyzer 1101. However, at steady state, the $CO_2$ upstream of the CO electrolyzer 1101 reacts with alkaline equivalents in the electrolyzer (see eq. 8-11 below), consuming alkaline equivalents in the electrolyzer and lowering the operating pH of the electrolyzer because bicarbonate and carbonate species are formed. This leads to large increases in the energy required to power the electrolysis process, and the formation of these anionic species and their salts leads to declines in electrolyzer performance and operational stability. The downstream subunits include an ethylene oxide synthesis and separation unit 1107 to recover vinyl acetate from the output stream departing the CO electrolyzer, a gas separation unit 1103 placed downstream of the gas/liquid separation unit 1102, and an alcohol removal system 1104 placed downstream of the liquid/gas separation subunit to recover alcohol products from the CO electrolyzer. Downstream of the alcohol removal subunit, a concentration and acidification unit 1105 converts the metal carboxylate products into carboxylic acid. The acidification subunit takes as an input an acid HX, such as hydrochloric acid HCl, which is converted into a metal salt MX, such as MCL, through the acidification of the input carboxylates. A liquid product separation method such as but not limited to distillation 1106 and/or solvent based extraction can be used to separate the carboxylic acid from the aqueous salt solution. MOH from the chlor-alkali electrolyzer 1108 is passed to the CO electrolyzer 1101. Gas separation unit 1112 downstream of the Ethylene oxide synthesis and separation unit 1107 separates CO and $CO_2$. Further, the $CO_2$ produced is used by $CO_2$ to CO upgrade system 1113 to produce CO.

$$CO_2 + OH^- \rightleftharpoons HCO_3^- \qquad (8)$$

$$CO_2 + H_2O \rightleftharpoons H_2CO_3 \qquad (9)$$

$$HCO_3^- + OH^- \rightleftharpoons CO_3^{2-} + H_2O \qquad (10)$$

$$HCO_3^- + H_2O \rightleftharpoons H_3O^+ + CO_3^{2-} \qquad (11)$$

A lower electrolyzer pH leads to higher energy requirements at the anode of a CO electrolyzer because non-precious anode materials such as but not limited to Ni, Co, Mn, Ti and even those made of precious materials such as Ir, Ru, Pt and Fe or their alloys with high activity, selectivity, and stability require higher driving forces to achieve the same current at low pH versus high pH. The cathode overpotential is also lower at high electrolyzer pH because the thermodynamic potential for CO reduction becomes more negative as pH rises. A lower electrolyte pH can also increase the proportion of current that produces dihydrogen at the cathode instead of reducing CO to more valuable products and alter the product distribution of the CO reduction products.

A CO electrolyzer in accordance with embodiments disclosed herein can have various architectures for the conversion of CO into valuable chemicals. The electrolyzer can include an anode area and a cathode area. CO can be provided to the anode area. The useful chemicals can be produced in the cathode area, in the anode area, or in a separating area located between the cathode area and the anode area of the electrolyzer. The electrolyzer can be a single planar electrolyzer. The electrolyzer can be a stack of cells. The cells in the stack can utilize bipolar plates. The bipolar plates can be charged to initiate reactions within the reactor. The electrolyzer can also be a filter press electrolyzer or a tubular electrolyzer.

In specific embodiments of the inventions disclosed herein, CO electrolyzers comprising a cathode area where CO reduction takes place according to equation 12 below and an anode area where an oxidation reaction takes place on an oxidation substrate, or an oxidation substrate/catalyst combination based on earth-abundant elements, precious elements, or combination of both. The oxidation substrate can be water, dihydrogen, halides, organic waste or any other oxidation substrate. For example, the oxidation reaction can involve water oxidation or dihydrogen oxidation according to equations 13 and 14 below, respectively.

$$xCO+(x+y-z)H_2O+(2x+y-2z)e^- \rightleftharpoons C_xH_yO_z+(2x+y-2z)OH^- \quad (12)$$

$$2H_2O \rightleftharpoons 4H^++4e^-+O_2 \quad (13)$$

$$H_2 \rightleftharpoons 2H^++2e^- \quad (14)$$

Both the CO and the oxidation substrate can be mixed with additive chemicals to alter the characteristics of the reactor and change the characteristics of the chemicals produced by the electrolyzer. CO electrolysis can be performed in various electrolyzers, including but not limited to flow-cell and membrane-electrode-assembly (MEA) electrolyzers. In flow-cell electrolyzers, reactant CO and electrolyte (water along with dissolved salts including but not limited to potassium hydroxide, sodium hydroxide, cesium hydroxide, lithium hydroxide) are decoupled by a gas diffusion electrode, thus overcoming the CO mass transport limitations and achieving industrially relevant production rates at the cathode. In flow-cell electrolyzer, the anodic reaction is an oxidation reaction, including but not limited to water oxidation, dihydrogen oxidation, chloride oxidation, halide oxidation, hydrocarbon oxidation, and waste organic oxidation. In the flow-cell electrolyzers, the cell is fed with electrolyte through both the anode and cathode compartments, or only through its anode compartment, or only through its cathode compartment. The anodic reaction can be performed on carbon (such as but not limited to carbon cloth, carbon paper, carbon felt) or metal-based substrates/catalysts including but not limited to Ir, Ni, Pt, Fe, Ti, Ru, Co. In zero-gap, membrane-electrode assembly electrolyzers, water vapor (either in the pure form or along with dissolved salts, including but not limited to potassium hydroxide, sodium hydroxide, cesium hydroxide) and reactant CO can be fed into the cathode inlet, while an oxidation substrate/catalyst such as water or dihydrogen is provided—optionally along with other species such as dissolved salts—on another connection coupled to an anode input of the electrolyzer.

The chemicals produced by the electrolyzer can vary in different embodiments of the invention. The chemicals can be separated using a separating element such as a trap for liquid chemicals on the anodic or cathodic output of the electrolyzer or a separating area between the cathode area and anode area which has its own output from the electrolyzer. The chemicals produced can be removed from the electrolyzer in solid or gaseous form and can be removed from the cathodic or anodic output streams on the cathode or anode outputs of the electrolyzer, or from a separate output using a separating layer/compartment. Examples of such a separating layer are provided below. A single electrolyzer can produce chemicals in gaseous form, liquid form, or both forms. Accordingly, the volume of chemicals generated could include at least one of a volume of hydrocarbons, a volume of organic acids, a volume of alcohols, a volume of olefins and a volume of N-rich organic compounds, where the chemicals are in gaseous, liquid, or both forms. For example, the volume of generated chemicals could include a volume of gaseous hydrocarbon and a volume of liquid alcohol. As another example, the volume of generated chemicals could include a volume of gaseous hydrocarbons and a volume of organic acids. As another example, the volume of generated chemicals could include a volume of gaseous hydrocarbons and a volume of alkali metal carboxylate salts. In a specific embodiment, the main targeted products are ethylene (in the gaseous product stream) and acetic acid/acetate (in the liquid product stream). In another embodiment, the main targeted products are ethylene (in the gaseous product stream) and ethanol (in the liquid product stream). In another embodiment, the main targeted products are n-propanol and ethanol (in the liquid product stream). In other embodiments, the oxidation reaction used at the anode is that of dihydrogen and such dihydrogen can be supplied from a hydrogen-generating system such as but not limited to the chlor-alkali electrolyzer.

In specific embodiments of the invention, a chlor-alkali electrolyzer is used to replenish hydroxide into the CO electrolyzer lost to processes including but not limited to dialysis or acetate formation. The chlor-alkali process is a mature technology used to produce hydroxide salts and chlorine gas at scale. A chlor-alkali electrolyzer contains a cathode performing water reduction to produce dihydrogen and hydroxide. In some embodiments, dioxygen is supplied to the cathode such that the cathode is performing a combination of water reduction and oxygen reduction. This reduces the cathode potential by reducing the overall current driven towards water reduction, which requires high cathode overpotential. A cathode which is performing both water reduction and oxygen reduction is called an oxygen depolarized cathode. The cathode is supplied with a caustic solution, which becomes more concentrated (10-35 wt % caustic) as it passes over the hydroxide generating cathode. The anode for a chlor-alkali electrolyzer is supplied with a pretreated brine solution, and chloride oxidation occurs at the electrode. The anode reaction typically occurs at a pH of approximately 2-4. Undesired water oxidation can also occur at the anode, but because water oxidation is a pH dependent reaction while chlorine oxidation is pH independent, chlorine oxidation is favored at low pH.

$$\text{Water reduction:} H_2O+2e^- \rightarrow H_2+2OH^- \quad (15)$$

$$\text{Oxygen reduction:} O_2+2H_2O+4e^- \rightarrow 4OH^- \quad (16)$$

$$\text{Chloride oxidation } 2Cl^- \rightarrow Cl_2+2e^- \quad (17)$$

$$\text{Water oxidation } 2H_2O \rightarrow O_2+4H^++4e^- \quad (18)$$

The cathode is composed of materials including but not limited to carbon steel, stainless steel, and nickel. The cathode may be coated with nickel-zinc, nickel aluminum, Raney nickel, nickel sulfur, coatings containing platinum, cobalt, or ruthenium, or other coatings to reduce the cathode overpotential. The anode substrate is composed of but not limited to graphite or titanium. In some embodiments, the titanium anode is coated with metal oxides such as but not limited to Ru and Ir, to reduce the overpotential and improve the lifetime of the anode. For oxygen depolarized cathodes, the cathode substrate must have hydrophobic properties to facilitate the transport of gaseous dioxygen to the surface of the cathode catalyst. The gas diffusion electrode may be home made as described above, or be one of the substrates from the following list: Sigracet 39AA, Sigracet 39BC, Sigracet 39BB, Sigracet 39BA, Sigracet 36AA, Sigracet 36BB, Sigracet 35BC, Sigracet 35BA, Sigracet 29BA, Sigracet 28BB, Sigracet 28AA, Sigracet 28BC, Sigracet 25BC, Sigracet 22BB, Sigracet 35BI, Toray papers, Toray THP-H-030, Toray TGP-H-060, Toray TGP-H-090, Toray TGP-H-120, Freudenberg H23C6, Freudenberg H15C13, Freudenberg H15C14, Freudenberg H14C10, Freudenberg H14CX483, Freudenberg H14CX653, Freudenberg H23C2, Freudenberg H23CX653, Freudenberg H24CX483, Freudenberg H23C6, Freudenberg H23C8, Freudenberg H24C5, Freudenberg H23C3, Avcarb MB-30, Avcarb GDS5130, Avcarb GDS2130, Avcarb GDS3250, Avcarb GDS3260, Avcarb GDS2230, Avcarb GDS2240, Avcarb GDS2255, Avcarb GDS2185, AvCar 1071, AvCarb 1698, AvCarbon1209, AvCarb 1185, AvCarb1186, AvCarb 7497, AvCarb T1819, AvCarb T1820, AvCarb T1824, AvCarbon 1071, AvCarb 1698, AvCarb 1209, AvCarb 1185, AvCarb 1186, AvCarb 1186, AvCarb T1819, AvCarb T1820, AvCarb T1824, AvCarb EP40, AvCarb P75, AvCarb EP55, AvCarbon EP40T, AvCarb P75T, AvCarb EP55T, AvCarb MGL190, AvCarb MGL280, AvCarbMGL370.

In a conventional chlor-alkali system, the input brine solution must be thoroughly pretreated before provisioning to the chlor-alkali anode to remove multivalent cations. Cation impurities can precipitate as salts in the membrane, separator, cathode, or anode, which is detrimental to cell voltage, current efficiency, and lifetime of the electrolyzer. Additionally, divalent cations can cause membrane fouling. Cation impurities that must be removed for sufficient electrolyzer performance include but are not limited to $Ca^{2+}$, $Mg^{2+}$, $Ba^{2+}$ $Fe^{3+}$, $Al^{3+}$ and heavy metals. The concentration of $Ca^{2+}$ and $Mg^{2+}$ should be a maximum of 20 ppb, while other cation impurities are typically purified to 0.1-4 ppm for a membrane chlor-alkali electrolyzer. The impurity concentrations for the brine feed for diaphragm chlor-alkali electrolyzer can be higher because the diaphragm does not foul during electrolysis. Impurities such as sulfates, chlorates, and silica also must be removed. Impurities are removed from the brine solution using methods including but not limited to chemical precipitation, clarification, ion exchange purification, submicron filtration, nanofiltration, precipitation using barium salts, ion exchange columns, acidification, and purging. After impurity removal, in some embodiments, hydrochloric acid is added to the brine to reduce its pH to 2-4 to minimize the formation of chlorates during electrolysis and to maximize the anodic selectivity for chlorine evolution. In a typical chlor-alkali process, a continuous supply of purified brine must be supplied to the electrolysis. In some embodiments of the invention, integrating the chlor-alkali system with a CO electrolyzer results in a situation where the costly brine purification must only be performed once because the $M^+$ is conserved in the process. Any consumed $Cl^-$ can be replenished into the brine in the form of HCl.

In some embodiments, the brine concentration must be purified such that the concentration of $Ca^{2+}$ and $Mg^{2+}$ is below 20 ppb, to achieve this from standard brine sources such as but not limited to rock salt, vacuum salt, sea salt, brine from well mining, or salt from waste incinerators, ion-exchange columns can be used. More specifically, once the salt has been dissolved in water and initially purified using precipitation, clarification, submicron filtration, and nanofiltration, it can be passed through an ion-exchange system consisting of several resin beds operating in series. When the first ion exchange resin bed (initially in the protonated form) is exhausted, the solution is passed through a second ion exchange resin bed. When the solution passes through the second ion exchange resin bed, the first exchanger is regenerated by treating it with acid such as but not limited to hydrochloric acid. The solution can pass between the ion exchangers until the concentration of cation impurities is below the threshold required for the process.

The anode and the cathode of the chlor-alkali electrolyzer can be separated by a membrane or a diaphragm. The diaphragm can be composed of materials such as but not limited to asbestos, zirconium oxide, poly(tetrafluoroethylene), polyethylene, polypropylene, and carbon fibers. In some embodiments, the separator is a cation exchange membrane which is designed to facilitate the transport of $M^+$ while minimizing the transport of OH. Additionally, this membrane can be durable under the conditions of electrolysis, exhibit low ion transport resistance and be mechanically robust. The permselectivity of the membrane is controlled by sulfonate functionalities, that preferentially transport $M^+$. Commercial cation exchange membranes typically used in chlor-alkali electrolyzers include but are not limited to Aciplex, Flemion, Nafion, and Aquivion membranes. In some embodiments, the membrane is reinforced with dispersed microfibers, PTFE, and fabrics. The membranes may also be coated in a nonconductive oxide, hydroxide, or carbide material to improve the hydrophilicity of the membrane and thus reduce the cell voltage. Using cation exchange membranes in a chlor-alkali electrolyzers, approximately 95% of the charge transferred is carried by $M^+$ with the remainder carried by $OH^-$.

Several cell designs have been employed for commercial chlor-alkali electrolyzers. In some embodiments, the CO electrolyzer is integrated with a membrane chlor-alkali electrolyzer with a cell design including but not limited to monopolar stacks, bipolar stacks, filter-press stacks, single element concept, zero-gap cell configurations, utilizing pressed electrodes in a zero-gap configuration, and using retractable cathodes and anodes. In other embodiments, the CO electrolyzer is integrated with a diaphragm chlor-alkali electrolyzer with a cell design including but not limited to rectangular vertical electrode cells, cylindrical vertical electrode cells, a Glanor electrolyzer, the Dow Cell, OxyTech "Hooker" Cells, HU monopolar cells, and OxyTech MDC Cells. The materials in the anode compartment consist of materials including but not limited to pure titanium and titanium alloys. The materials in the cathode compartment consist of materials including but not limited to stainless steel, nickel, and titanium.

The concentrated caustic that exits the cathode of the chlor-alkali cell has a low chloride concentration for most commercial applications or to provision into a CO electrolyzer. The caustic product from a diaphragm chlor-alkali electrolyzer can contain 0.5-2 wt % MCl, and in some embodiments, must be purified further. In a membrane chlor-alkali electrolyzer, diffusion of chloride from the anodic compartment to the cathodic compartment is limited, so concentrations of chloride are as low as 20 ppm. To remove the chloride from the caustic product in a diaphragm cell, the liquid containing MOH and MCl can be concentrated in an evaporator until the solution is ~50% in MOH, after which fractional crystallization is performed to remove the MCl. For purifying the caustic further, liquid ammonia can be added to absorb salt, chlorates, and other impurities. The liquid ammonia must then be stripped from the caustic solution. Removal of chloride from either the membrane process or the diaphragm process may also proceed through processes including but not limited to ion exchange purification, nanofiltration, precipitation using barium salts, chemical precipitation, ion exchange columns, reverse osmosis, electrodialysis, and diffusion dialysis.

The ethylene dichloride and vinyl chloride process units downstream of the CO electrolyzer operate as follows. In brief, ethylene dichloride is produced by the reaction of ethylene with either chlorine gas and/or hydrochloric acid and dioxygen. In the direct reaction of ethylene with chlorine gas, a Lewis acid such as iron (III) chloride used as a catalyst in the liquid phase according to equation 19. In some cases, dioxygen is added to the reaction mixture.

$$C_2H_4 + Cl_2 \rightarrow C_2H_2Cl_2 \quad (19)$$

The oxychlorination of ethylene to form ethylene dichloride involves the reaction of ethylene with hydrogen chloride and oxygen, using Cu(II) as a catalyst at temperatures ranging from 100 to 400° C., according to equation 20. Other catalysts and additives such as but not limited to those including alkali metals, alkaline earth metals, and metallic compounds can also be used in the reactor to improve efficiency. Supports such as but not limited to alumina, carbon, silica, and other high surface area porous materials can be used to improve the reaction efficiency. The system pressure can be varied between 1 to 20 bar. A side reaction of ethylene oxychlorination is the combustion and/or steam reforming of ethylene to form CO or $CO_2$ (equation 20-24).

$$C_2H_4 + 2HCl + \tfrac{1}{2}O_2 \rightarrow C_2H_2Cl_2 + H_2O \quad (20)$$

$$C_2H_4 + 3O_2 \rightarrow 2CO_2 + 2H_2O \quad (21)$$

$$C_2H_4 + 2O_2 \rightarrow 2CO + 2H_2O \quad (22)$$

$$C_2H_4 + H_2O \rightarrow 2CO + 3H_2 \quad (23)$$

$$C_2H_4 + 4H_2O \rightarrow 2CO_2 + 6H_2 \quad (24)$$

Downstream of the chlorination unit, separators using technologies such as but not limited to membrane-based adsorption, pressure and temperature swing adsorption, and distillation are used to purify the ethylene dichloride product. In the direct chlorination process, unreacted ethylene is recirculated back into the reactor after condensation. Ethylene dichloride is collected in a condenser.

Following the production of ethylene dichloride, vinyl chloride and hydrochloric acid can be co-produced via the thermal cracking of ethylene dichloride, a process summarized in equation 25. The reaction is typically performed in the gas phase and a catalyst can be used in some cases. The catalyst used can include but is not limited to ammonium salts, carbon, silicates, alumina compounds, salts, zeolites, and other ceramics. The reaction temperature can be varied between 30° and 700° C., with the reactor pressure varied between 1 to 50 bar.

$$C_2H_2Cl_2 \rightarrow C_2H_3Cl + HCl \quad (25)$$

Downstream of the vinyl chloride cracking unit, cooling and separation units can be used to obtain a purified product. A combination of one or more separation techniques and units can be used, such as but not limited to distillation, filtration, and adsorption of the furnace product to remove impurities such as but not limited to hydrocarbons such as ethylene, acetylene, benzene, vinylacetylene, and chlorinated organic compounds. Carbonaceous deposits formed from side reactions can be removed using filters.

The separating steps and processes described above can take on various forms. The separation system may conduct one or more of multiple separation/purification steps including any technology available for the targeted purification/ separation. The separation system can include separation units based on but not limited to membrane technologies including but not limited to dense polymeric membranes, ultrafiltration and nano-filtration membranes, facilitated-transport membranes, metallic membranes, zeolite membranes, ceramic proton conducting membranes hollow fiber pervaporation membranes, carbon molecular sieve (CMS) membranes, cryogenic technologies, adsorption technologies including but not limited to physisorption and chemisorption based technologies, absorption technologies, including physical absorption technologies and chemical absorption technologies, with operation techniques such as but not limited to vacuum pressure swing, temperature swing, pressure swing, arid pressure swing, coupled pressure and temperature swing, and electric swing. Chemical adsorbents that can be used include but are not limited to amine-based adsorbents (amine grafted or impregnated solids), metal oxides, metal salts, double salts and hydrotalcites. Physical adsorbents that can be used include but are not limited to materials such as carbon-based materials as activated carbon or carbon molecular sieve, mesoporous silica, activated alumina, zeolites, zeolitic imidazolate frameworks (ZIFs), metalorganic frameworks (MOFs), covalent organic frameworks (COFs), and blended adsorbents.

Swing adsorption techniques are used to physically or chemically adsorb species in a fluid line in order to separate it from other gases. Swing adsorption is generally non-oxidative to the CO and dihydrogen present in the gas stream. Such techniques use an adsorbent selective for one or more of the molecules in a fluid line and achieve separation through the following steps: the first is the adsorption of the one species, while all other species pass through the adsorbent, and the second is a regeneration, wherein an increase in temperature or/and a decrease in pressure is used to extract the adsorbed species from the adsorbent material. Several swing adsorption separators, usually between two and ten, may be operated in parallel, allowing continuous separation and minimizing the specific power consumption. The adsorbent material can operate via a chemical or physical mechanism. Chemical adsorbents that can be used include, but are not limited to, amine-based adsorbents (amine grafted or impregnated solids), metal oxides, metal salts, double salts and hydrotalcites. Physical adsorbents that can be used include but are not limited to materials such as activated carbons, carbon molecular sieves, mesoporous silica, zeolites, zeolitic imidazolate frameworks (ZIFs), metal organic frameworks (MOFs), or blended adsorbents. Swing adsorption processes can be applied to, but not limited to, $CO_2$ removal, oxygen removal, carbon oxide/dihydrogen separation, nitrogen removal, volatile organic chemical removal, methane/carbon oxide separation, gas drying and a mix of the previous applications according to the sorbent material nature, number of different sorbent layers and the operating conditions.

Membrane separation uses an extended surface comprising a polymeric species for the movement/restriction of a particular species in a fluid line. Membrane separation is generally non-oxidative to the CO and dihydrogen present in the gas stream. The separator may comprise several layers of the membrane surface to achieve effective separation. At commercial scale, membranes can be arranged, in a hollow fiber module, in a spiral wound module, and other modules. The separation is achieved through a favorable chemical interaction of the membrane with the substance to be removed from the fluid line or through a size of pore tailored for the exclusion of larger molecules within the fluid. The different gas species either end on the permeate side, meaning they have gone through the membrane layers leading to pressure drops, or in the retentate side. The separation driving force can be the pressure gradient or/and the concentration gradient between the permeate and the retentate side. These processes may require several independent stages of compressor and membrane units to achieve full purification of the fluid line and to reach the largest recovery rate of the desired species. Membranes can be applied to $CO_2$ removal, oxygen removal, nitrogen removal, dihydrogen/CO separation, olefin removal, gas drying and a mix of the previous application according to the membrane material, the number of membrane stages and the operating conditions.

The CO gas mixture to be purified and fed into to the CO electrolyzer, depending on the production process, can be water saturated at the stream pressure and temperature or relative humidity can be as high as 80%-100% at the considered pressure and temperature. To avoid water condensation in pipes, gas compressors, process units, water can be fully or partially removed until a defined temperature dew point. Pipes and process units can be insulated, or heat traced (electrically or through sealed envelope). Several processes can be used to remove water such as but not limited to: (1) a heat exchanger using cool refrigerant to condense water; (2) a physical absorption unit using physical solvents such as, but not limited to, methanol, glycol (e.g., monoethylene glycol (MEG), diethylene glycol (DEG), triethylene glycol (TEG), or tetraethylene glycol (TREG)); (3) a membrane based processes which is selective for water removal; and (4) an adsorption filter using sorbent such as, but not limited to, activated alumina, zeolite (3A, 4A), and silica gel. Solution (1) cannot reduce the gas water dew point below 0-5° C. Solution (2), (3) and (4) can reduce the gas water dew point between −10° C. and −50° C. meaning less than 10 ppm of water.

CO-rich gas can be compressed, upstream or downstream the separation units, prior to introduction into the electrolyzer. Compressor technologies that can be used include centrifugal or volumetric technologies. Volumetric technologies include, but are not limited to, membrane compressors, screw compressors, and reciprocating compressors. The technology choice depends on the gas flowrate and on the required outlet pressure. Knowing that the maximum compression ratio through a compressor is commonly taken at 3, between 1 and 5 compression stages may be needed to reach the required pressure. Inter-stage cooling steps may then be necessary.

Figure 12:
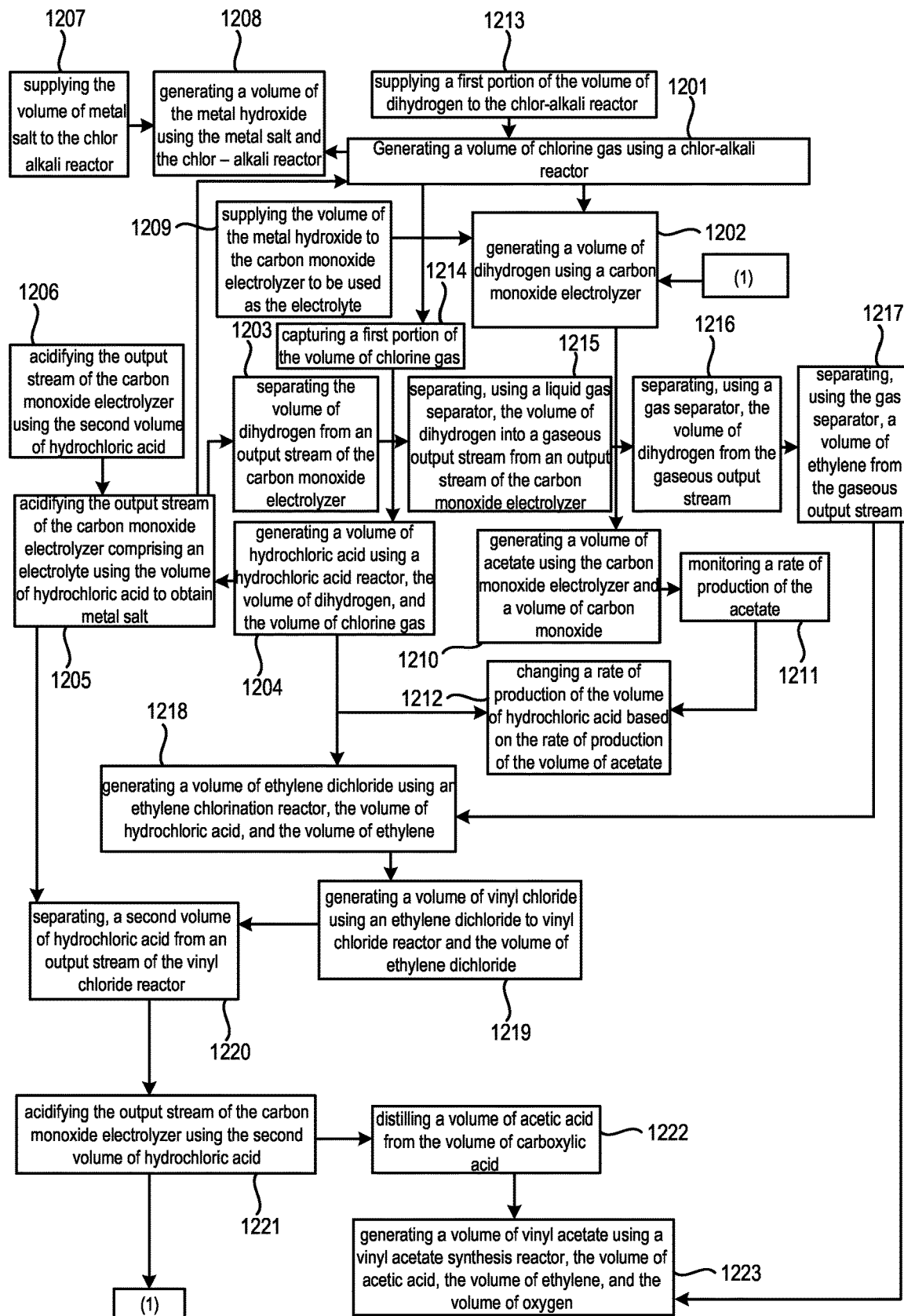
FIG. 12 illustrates a flowchart for a set of processes involving the generation of hydrochloric acid using an integrated chlor-alkali electrolyzer and CO electrolyzer in accordance with specific embodiments of the inventions disclosed herein.

Specific embodiments of the inventions disclosed herein provide a method for hydrochloric acid production utilizing the products from both reactors, i.e., a CO electrolyzer and a chlor-alkali electrolyzer. The process comprises the steps of generating a volume of metal hydroxide and a volume of chlorine gas using a chlor-alkali reactor 1201 (see, for example, FIG. 12); generating a volume of dihydrogen using a carbon monoxide electrolyzer 1202; separating the volume of dihydrogen from an output stream of the carbon monoxide electrolyzer 1203; and generating a volume of hydrochloric acid using a hydrochloric acid reactor, the volume of dihydrogen, and the volume of chlorine gas 1204.

Specific embodiments of the inventions disclosed herein provide a method used to acidify the output stream of the carbon monoxide electrolyzer using the volume of hydrochloric acid 1205, wherein (i) the output stream includes a volume of carboxylates; and (ii) the acidifying of the output stream converts the volume of carboxylates to a volume of carboxylic acid.

In the process, the metal is circulated by acidifying an output stream of the carbon monoxide electrolyzer using the volume of hydrochloric acid, wherein the output stream includes an electrolyte 1206, wherein the electrolyte is a metal hydroxide, and whereby the metal hydroxide in the output stream is converted into a volume of the metal salt; supplying the volume of metal salt to the chlor-alkali reactor 1207; generating a volume of the metal hydroxide using the metal salt and the chlor-alkali reactor 1208; and supplying the volume of the metal hydroxide to the carbon monoxide electrolyzer to be used as the electrolyte 1209.

Further, the production of the products is balanced by generating a volume of acetate using the carbon monoxide electrolyzer and the volume of carbon monoxide 1210; monitoring a rate of production of the acetate 1211; and changing a rate of production of the volume of hydrochloric acid based on the rate of production of the volume of acetate 1212, wherein the rate of production of the volume of hydrochloric acid is increased when the rate of production of the acetate increases, and wherein the rate of production of the volume of hydrochloric is decreased when the rate of production of the acetate decreases.

Specific embodiments of the inventions disclosed herein include a method comprising supplying a first portion of the volume of dihydrogen to the chlor-alkali reactor 1213; wherein: (i) the generating of the hydrochloric acid uses a second portion of the volume of dihydrogen; and (ii) the changing of the rate of production of the volume of hydrochloric acid includes changing the first portion relative to the second portion.

The method further comprises capturing a first portion of the volume of chlorine gas 1214 such that (i) the generating of the hydrochloric acid uses a second portion of the volume of chlorine gas; and (ii) the changing of the rate of production of the volume of hydrochloric acid includes changing the first portion relative to the second portion.

The method for harvesting dihydrogen comprises separating, using a liquid-gas separator, the volume of dihydrogen into a gaseous output stream from an output stream of the carbon monoxide electrolyzer 1215; and separating, using a gas separator, the volume of dihydrogen from the gaseous output stream 1216.

Specific embodiments of the inventions disclosed herein provide for production of vinyl chloride by separating, using the gas separator, a volume of ethylene from the gaseous output stream 1217; generating a volume of ethylene dichloride using an ethylene chlorination reactor, the volume of hydrochloric acid, and the volume of ethylene 1218; and generating a volume of vinyl chloride using an ethylene dichloride to vinyl chloride reactor and the volume of ethylene dichloride 1219. Enough hydrochloric acid is produced for the output stream of CO electrolyzer to convert the carboxylate to acid and for generating ethylene dichloride. Further, separating a second volume of hydrochloric acid from an output stream of the vinyl chloride reactor 1220; and acidifying the output stream of the carbon monoxide electrolyzer using the second volume of hydrochloric acid 1221; such that (i) the output stream of the carbon monoxide electrolyzer includes a volume of carboxylates; and (ii) the acidifying of the output stream of the carbon monoxide electrolyzer converts the volume of carboxylates to a volume of carboxylic acid. Enough hydrochloric acid is produced for the output stream of CO electrolyzer to recycle the metal and for generating ethylene dichloride.

In further specific embodiments of the present invention, a method comprises separating, a second volume of hydrochloric acid from an output stream of the vinyl chloride reactor 1220; and acidifying an output stream of the carbon monoxide electrolyzer using the second volume of hydrochloric acid 1221, wherein the output stream includes an electrolyte, wherein the electrolyte is a metal hydroxide, and whereby the metal hydroxide in the output stream is converted into a volume of the metal salt; supplying the volume of metal salt to the chlor-alkali reactor 1207; generating a volume of the metal hydroxide using the metal salt and the chlor-alkali reactor 1208; and supplying the volume of the metal hydroxide to the carbon monoxide electrolyzer to be used as the electrolyte 1209.

In another embodiment of the present invention, a process for the preparation of vinyl acetate is provided by acidifying the output stream of the carbon monoxide electrolyzer using the volume of hydrochloric acid 1221, wherein: (i) the output stream includes a volume of carboxylates; and (ii) the acidifying of the output stream converts the volume of carboxylates to a volume of carboxylic acid; distilling a volume of acetic acid from the volume of carboxylic acid 1222; and generating a volume of vinyl acetate using a vinyl acetate synthesis reactor, the volume of acetic acid, the volume of ethylene, and the volume of oxygen 1223.

Figure 13:
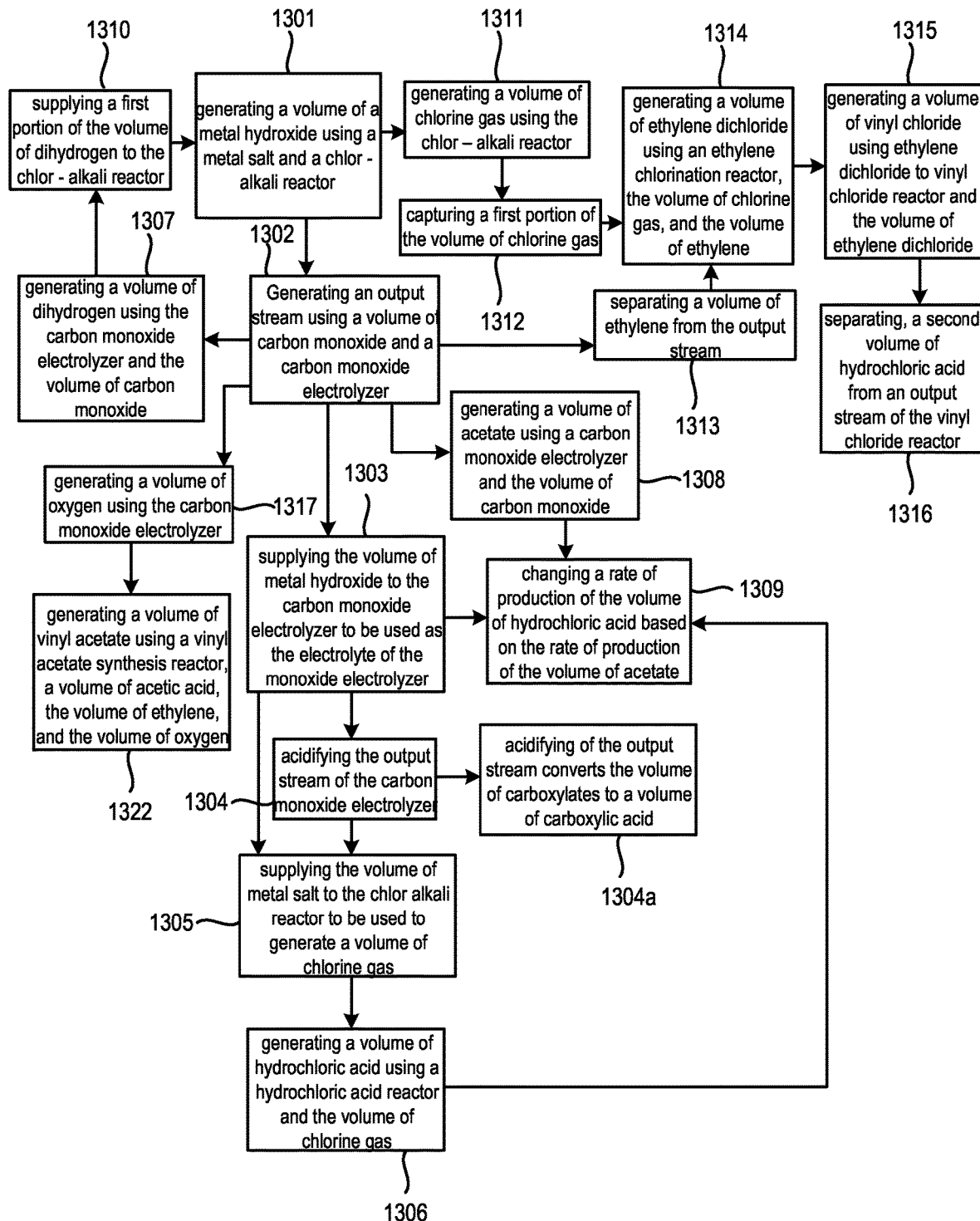
FIG. 13 illustrates a flowchart for a set of processes involving the circulation of the electrolyte for a CO electrolyzer integrated with a chlor-alkali electrolyzer in accordance with specific embodiments of the inventions disclosed herein.

In another embodiment of the present invention a method for refreshing the electrolyte of the CO electrolyzer is provided which comprises generating a volume of a metal hydroxide using a metal salt and a chlor-alkali reactor 1301 (see, for example, FIG. 13); generating an output stream using a volume of carbon monoxide and a carbon monoxide electrolyzer 1302, wherein the metal hydroxide is an electrolyte of the carbon monoxide electrolyzer; supplying the volume of metal hydroxide to the carbon monoxide electrolyzer to be used as the electrolyte of the carbon monoxide electrolyzer 1303; acidifying the output stream of the carbon monoxide electrolyzer, wherein the output stream includes the electrolyte 1304, and whereby the metal hydroxide in the output stream is converted into a volume of the metal salt; and supplying the volume of metal salt to the chlor-alkali reactor to be used to generate a volume of chlorine gas 1305.

In a further another embodiment of the present invention the metal is circulated, and the carboxylate is acidified, the output stream includes a volume of carboxylates; and the acidifying of the output stream converts the volume of carboxylates to a volume of carboxylic acid 1304a.

In another embodiment of the present invention, the metal is circulated, and an acid is generated using chlorine gas from chlor-alkali by generating a volume of hydrochloric acid using a hydrochloric acid reactor 1306 and the volume of chlorine gas; wherein the acidifying of the output stream is conducted using the volume of hydrochloric acid.

In a further another embodiment of the present invention, the metal is circulated, and acid is generated using combination from reactors by generating a volume of dihydrogen using the carbon monoxide electrolyzer and the volume of carbon monoxide 1307; wherein the generating of the hydrochloric acid using the hydrochloric acid reactor uses the volume of dihydrogen.

In another embodiment of the present invention circulation of the metal is performed and the production is balanced by generating a volume of hydrochloric acid using a hydrochloric acid reactor 1306; generating a volume of acetate using a carbon monoxide electrolyzer and the volume of carbon monoxide 1308; and changing a rate of production of the volume of hydrochloric acid based on the rate of production of the volume of acetate 1309, wherein the rate of production of the volume of hydrochloric acid is increased when the rate of production of the acetate increases, and wherein the rate of production of the volume of hydrochloric acid is decreased when the rate of production of the acetate decreases.

In a further embodiment of the present invention, specific embodiments of the present invention provide for generating the volume of dihydrogen using the carbon monoxide electrolyzer and the volume of carbon monoxide 1307; and supplying a first portion of the volume of dihydrogen to the chlor-alkali reactor 1310 wherein: (i) the generating of the hydrochloric acid uses a second portion of the volume of dihydrogen; and (ii) the changing of the rate of production of the volume of hydrochloric acid includes changing the first portion relative to the second portion.

Further, specific embodiments of the present invention provide for generating a volume of chlorine gas using the chlor-alkali reactor 1311; capturing a first portion of the volume of chlorine gas 1312; wherein: (i) the generating of the hydrochloric acid uses a second portion of the volume of chlorine gas; and (ii) the changing of the rate of production of the volume of hydrochloric acid includes changing the first portion relative to the second portion.

In another embodiment of the present invention, vinyl chloride is produced by generating a volume of chlorine gas using the chlor-alkali reactor 1311; separating a volume of ethylene from the output stream 1313; generating a volume of ethylene dichloride using an ethylene chlorination reactor, the volume of chlorine gas, and the volume of ethylene 1314; and generating a volume of vinyl chloride using an ethylene dichloride to vinyl chloride reactor and the volume of ethylene dichloride 1315.

Specific embodiments of the present invention provide for recycling metal using a second volume of hydrochloric acid from an output stream of the vinyl chloride reactor 1316; and whereby the acidifying of the output stream of the carbon monoxide electrolyzer uses the second volume of hydrochloric acid.

In a further embodiment, the metal is recycled and vinyl acetate is produced by generating a volume of oxygen using the carbon monoxide electrolyzer 1317; separating a volume of ethylene from the output stream 1313; generating a volume of vinyl acetate using a vinyl acetate synthesis reactor, a volume of acetic acid, the volume of ethylene, and the volume of oxygen 1322; wherein: (i) the output stream includes a volume of carboxylates; and (ii) the acidifying of the output stream converts the volume of carboxylates to a volume of carboxylic acid; (iii) the volume of acetic acid is distilled from the volume of carboxylic acid.

Figure 14:
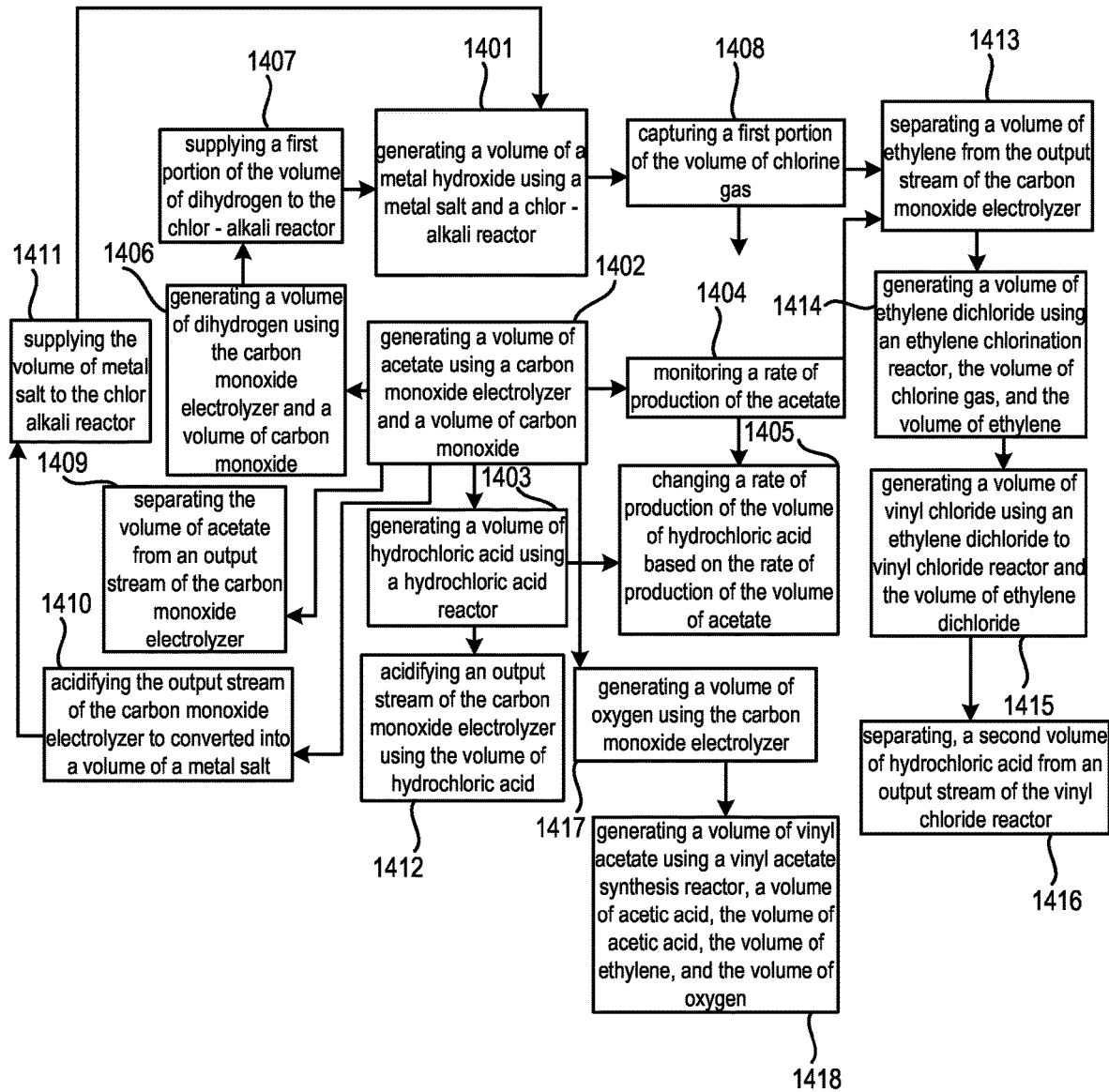
FIG. 14 illustrates a flowchart for a set of processes for balancing acid production based on acetate production in accordance with specific embodiments of the inventions disclosed herein.

Further specific embodiments of the invention provide for a balancing of acid production based on acetate production performed by generating a volume of chlorine gas using a chlor-alkali reactor 1401 (see, for example, FIG. 14); generating a volume of acetate using a carbon monoxide electrolyzer and a volume of carbon monoxide 1402; generating a volume of hydrochloric acid using a hydrochloric acid reactor 1403; monitoring a rate of production of the acetate 1404; and changing a rate of production of the volume of hydrochloric acid based on the rate of production of the volume of acetate 1405, wherein the rate of production of the volume of hydrochloric acid is increased when the rate of production of the acetate increases, and wherein the rate of production of the volume of hydrochloric acid is decreased when the rate of production of the acetate decreases.

Further, specific embodiments of the present invention provides generating a volume of dihydrogen using the carbon monoxide electrolyzer and the volume of carbon monoxide 1406; and supplying a first portion of the volume of dihydrogen to the chlor-alkali reactor 1407; wherein: (i) the generating of the volume of hydrochloric acid uses a second portion of the volume of dihydrogen; and (ii) the changing of the rate of production of the volume of hydrochloric acid includes changing the first portion relative to the second portion. A first portion of the volume of chlorine gas 1408 is captured; wherein: (i) the generating of the hydrochloric acid uses a second portion of the volume of chlorine gas; and (ii) the changing of the rate of production of the volume of hydrochloric acid includes changing the first portion relative to the second portion.

In another embodiment of the present invention, a method includes generating the volume of dihydrogen using the carbon monoxide electrolyzer and a volume of carbon monoxide 1406; and wherein the generating of the volume of hydrochloric acid uses the volume of dihydrogen.

Further, a method is provided which includes separating the volume of acetate from an output stream of the carbon monoxide electrolyzer 1409, wherein the output stream includes an electrolyte of the electrolyzer, and wherein the electrolyte is a metal hydroxide; acidifying the output stream of the carbon monoxide electrolyzer, wherein the output stream includes the electrolyte 1410, and whereby the metal hydroxide in the output stream is converted into a volume of a metal salt; and supplying the volume of metal salt to the chlor-alkali reactor 1411.

Further, in another embodiment of the present invention, acetic acid is produced by acidifying an output stream of the carbon monoxide electrolyzer using the volume of hydrochloric acid 1412; wherein (i) the output stream includes a volume of acetate; and (ii) the acidifying of the output stream converts the volume of acetate to a volume of acetic acid.

Further, vinyl chloride is produced by generating a volume of chlorine gas using the chlor-alkali reactor 1401; separating a volume of ethylene from the output stream 1413; generating a volume of ethylene dichloride using an ethylene chlorination reactor, the volume of chlorine gas, and the volume of ethylene 1414; and generating a volume of vinyl chloride using an ethylene dichloride to vinyl chloride reactor and the volume of ethylene dichloride 1415.

Further, a method is provided which includes acidifying the output stream by separating, a second volume of hydrochloric acid from an output stream of the vinyl chloride reactor 1416; and acidifying the output stream of the carbon monoxide electrolyzer using the second volume of hydrochloric acid 1412; wherein: (i) the output stream includes a volume of acetate; and (ii) the acidifying of the output stream converts the volume of acetate to a volume of acetic acid.

In a further embodiment of the present invention, vinyl acetate is produced by acidifying the output stream of the carbon monoxide electrolyzer using the volume of hydrochloric acid 1412; generating a volume of oxygen using the carbon monoxide electrolyzer 1417; separating a volume of ethylene from an output stream 1413 of the carbon monoxide electrolyzer; and generating a volume of vinyl acetate using a vinyl acetate synthesis reactor, a volume of acetic acid, the volume of ethylene, and the volume of oxygen 1418; wherein: (i) the output stream includes the volume of acetate; and (ii) the acidifying of the output stream converts the volume of acetate to the volume of acetic acid.

Figure 15:
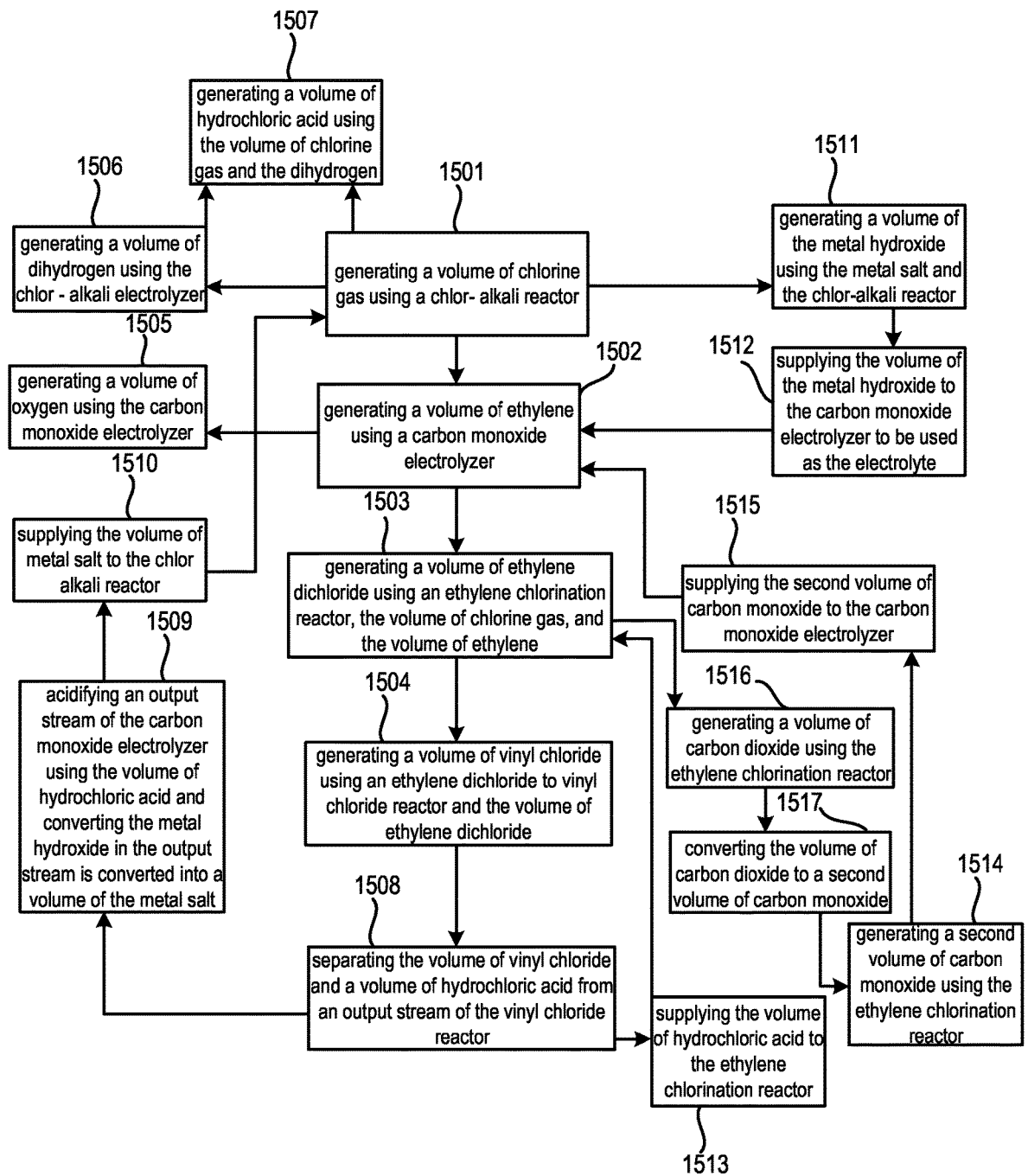
FIG. 15 illustrates a flowchart for a set of processes for vinyl chloride production in accordance with specific embodiments of the inventions disclosed herein.

In another embodiment of the present invention, vinyl chloride is produced by generating a volume of chlorine gas using a chlor-alkali reactor 1501 (see, for example, FIG. 15); generating a volume of ethylene using a carbon monoxide electrolyzer 1502; generating a volume of ethylene dichloride using an ethylene chlorination reactor, the volume of chlorine gas, and the volume of ethylene 1503; and generating a volume of vinyl chloride using an ethylene dichloride to vinyl chloride reactor and the volume of ethylene dichloride 1504.

In another embodiment of the present invention, the method comprises generating a volume of oxygen using the carbon monoxide electrolyzer 1505; generating a volume of dihydrogen using the chlor-alkali electrolyzer 1506; and generating a volume of hydrochloric acid using the volume of chlorine gas and the volume of dihydrogen 1507; wherein the generating of the ethylene dichloride uses the volume of chlorine gas in that the ethylene chlorination reactor is supplied with the volume of hydrochloric acid.

Further, in another embodiment, the method comprises generating the volume of dihydrogen using the chlor-alkali electrolyzer 1506; and generating the volume of hydrochloric acid using the volume of chlorine gas and the volume of dihydrogen 1507; wherein the generating of the ethylene dichloride uses the volume of chlorine gas in that the ethylene chlorination reactor is supplied with the volume of hydrochloric acid.

Further, the method comprises separating the volume of vinyl chloride and a volume of hydrochloric acid from an output stream of the vinyl chloride reactor 1508; and acidifying an output stream of the carbon monoxide electrolyzer using the volume of hydrochloric acid, wherein the output stream includes a volume of carboxylates, and whereby the acidifying of the output stream of the carbon monoxide electrolyzer converts the volume of carboxylates to a volume of carboxylic acid.

In a further another embodiment of the present invention, the method comprises the steps of separating the volume of vinyl chloride and a volume of hydrochloric acid from an output stream of the vinyl chloride reactor 1508; and acidifying an output stream of the carbon monoxide electrolyzer, wherein the output stream includes an electrolyte, wherein the electrolyte is a metal hydroxide, and whereby the metal hydroxide in the output stream is converted into a volume of the metal salt 1509; supplying the volume of metal salt to the chlor-alkali reactor 1510; generating a volume of the metal hydroxide using the metal salt and the chlor-alkali reactor 1511; and supplying the volume of the metal hydroxide to the carbon monoxide electrolyzer to be used as the electrolyte 1512.

Further another embodiment of the present invention provides generating the volume of oxygen using the carbon monoxide electrolyzer 1505; wherein the generating of the ethylene dichloride uses the volume of oxygen. A volume of oxygen using the carbon monoxide electrolyzer 1505 is generated; wherein the generating of the ethylene dichloride and the chlor-alkali reactor both use the volume of oxygen.

Further, a method of an embodiment of the present invention comprises separating the volume of vinyl chloride and a volume of hydrochloric acid from an output stream of the vinyl chloride reactor 1508; and supplying the volume of hydrochloric acid to the ethylene chlorination reactor 1513.

The method comprises generating a second volume of carbon monoxide using the ethylene chlorination reactor 1514; and supplying the second volume of carbon monoxide to the carbon monoxide electrolyzer 1515. A volume of carbon dioxide is generated using the ethylene chlorination reactor 1516, converting the volume of carbon dioxide to a second volume of carbon monoxide 1517; and supplying the second volume of carbon monoxide to the carbon monoxide electrolyzer 1515.

Figure 16:
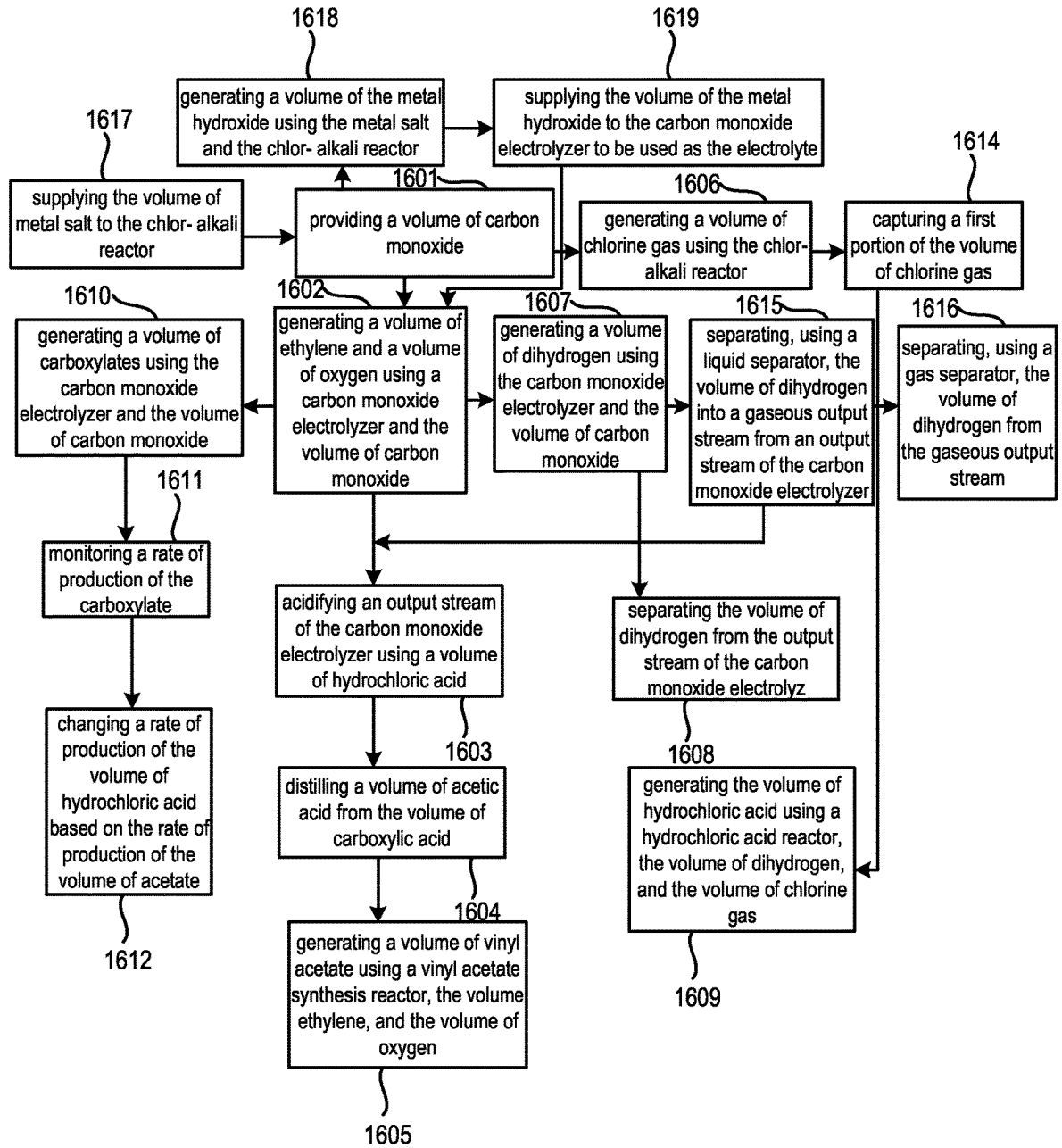
FIG. 16 illustrates a flowchart for a set of processes for vinyl acetate production in accordance with specific embodiments of the inventions disclosed herein.

In a further embodiment of the present invention, the present invention provides a method for the preparation of vinyl acetate by providing a volume of carbon monoxide 1601 (see, for example, FIG. 16); generating a volume of ethylene and a volume of oxygen using a carbon monoxide electrolyzer and the volume of carbon monoxide 1602; acidifying an output stream of the carbon monoxide electrolyzer using a volume of hydrochloric acid 1603, wherein the output stream includes a volume of carboxylates, and whereby the acidifying of the output stream of the carbon monoxide electrolyzer converts the volume of carboxylates to a volume of carboxylic acid; distilling a volume of acetic acid from the volume of carboxylic acid 1604; and generating a volume of vinyl acetate using a vinyl acetate synthesis reactor, the volume of acetic acid, the volume of ethylene, and the volume of oxygen 1605.

In another embodiment of the present invention, the present invention provides a method for the preparation of hydrochloric acid by the integrated electrolyzers by generating a volume of chlorine gas using the chlor-alkali reactor 1606; generating a volume of dihydrogen using the carbon monoxide electrolyzer and the volume of carbon monoxide 1607; separating the volume of dihydrogen from the output stream of the carbon monoxide electrolyzer 1608; and generating the volume of hydrochloric acid using a hydrochloric acid reactor, the volume of dihydrogen, and the volume of chlorine gas 1609.

In a further embodiment of the present invention, the production is balanced by generating a volume of carboxylates using the carbon monoxide electrolyzer and the volume of carbon monoxide 1610; monitoring a rate of production of the carboxylate 1611; and changing a rate of production of the volume of hydrochloric acid based on the rate of production of the volume of acetate 1612, wherein the rate of production of the volume of hydrochloric is increased when the rate of production of the carboxylate increases, and wherein the rate of production of the volume of hydrochloric acid is decreased when the rate of production of the carboxylate decreases.

Further, the method comprises the steps of supplying a first portion of the volume of dihydrogen to the chlor-alkali reactor; wherein: (i) the generating of the hydrochloric acid uses a second portion of the volume of dihydrogen; and (ii) the changing of the rate of production of the volume of hydrochloric acid includes changing the first portion relative to the second portion. Further, the method comprises capturing a first portion of the volume of chlorine gas 1614; wherein: (i) the generating of the hydrochloric acid uses a second portion of the volume of chlorine gas; and (ii) the changing of the rate of production of the volume of hydrochloric acid includes changing the first portion relative to the second portion.

Further, dihydrogen is harvested in embodiments of the present invention by separating, using a liquid-gas separator, the volume of dihydrogen into a gaseous output stream from an output stream of the carbon monoxide electrolyzer 1615; and separating, using a gas separator, the volume of dihydrogen from the gaseous output stream 1616.

In a further embodiment of the present invention, acidification is used to circulate the electrolyte of the CO electrolyzer where the output stream includes an electrolyte; the electrolyte is a metal hydroxide; and where acidifying the output stream of the carbon monoxide electrolyzer using the volume of hydrochloric acid 1603 converts the metal hydroxide in the output stream into a volume of the metal salt; and the method further comprises: supplying the volume of metal salt to the chlor-alkali reactor 1617; generating a volume of the metal hydroxide using the metal salt and the chlor-alkali reactor 1618; and supplying the volume of the metal hydroxide to the carbon monoxide electrolyzer to be used as the electrolyte 1619.

Figure 17:
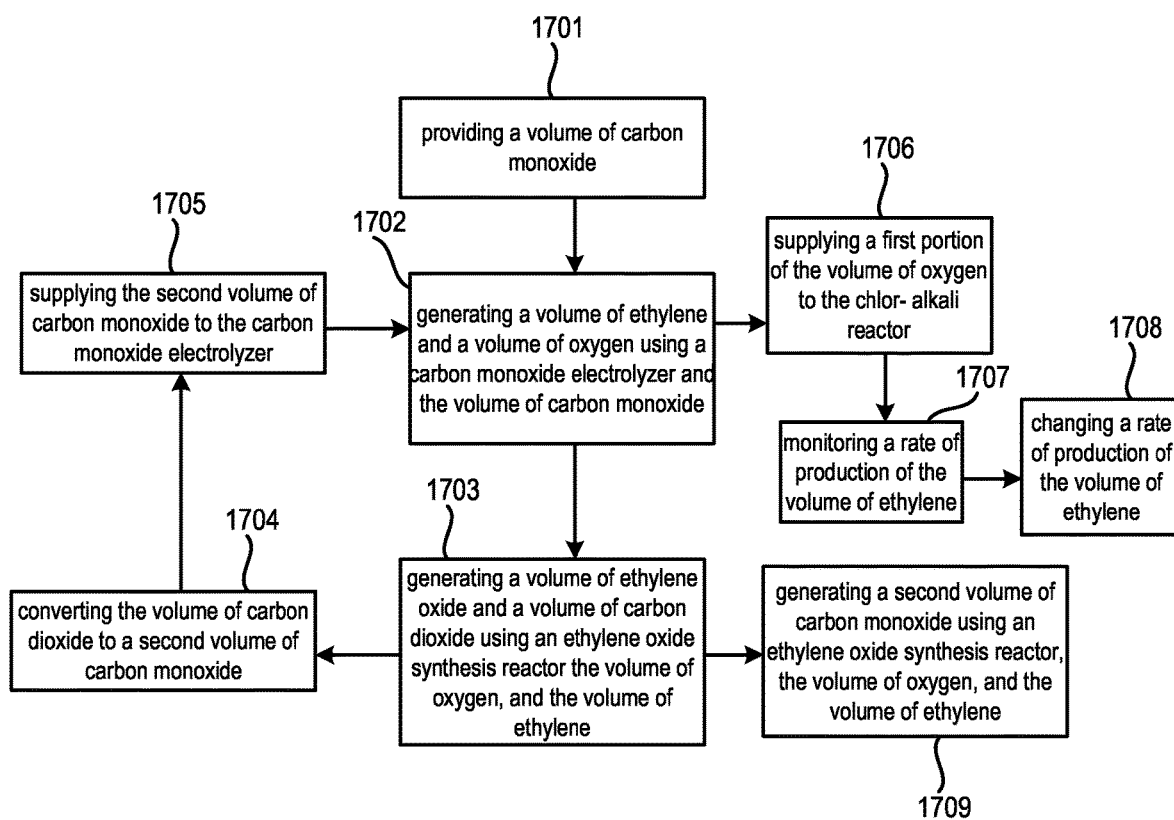
FIG. 17 illustrates a flowchart for a set of processes for ethylene oxide production in accordance with specific embodiments of the inventions disclosed herein.

In a further another embodiment of the present invention, ethylene oxide is produced by providing a volume of carbon monoxide 1701 (see, for example, FIG. 17); generating a volume of ethylene and a volume of oxygen using a carbon monoxide electrolyzer and the volume of carbon monoxide 1702; generating a volume of ethylene oxide and a volume of carbon dioxide using an ethylene oxide synthesis reactor, the volume of oxygen, and the volume of ethylene 1703, converting the volume of carbon dioxide to a second volume of carbon monoxide 1704; and supplying the second volume of carbon monoxide to the carbon monoxide electrolyzer 1705. Further, supplying a first portion of the volume of oxygen to the chlor-alkali reactor 1706; monitoring a rate of production of the volume of ethylene 1707; changing a rate of production of the volume of ethylene 1708; wherein: (i) the generating of the ethylene oxide synthesis uses a second portion of the volume of oxygen; and (ii) the changing of the rate of production of the volume of ethylene includes changing the first portion relative to the second portion. Further, generating a second volume of carbon monoxide using an ethylene oxide synthesis reactor, the volume of oxygen, and the volume of ethylene 1709; and supplying the second volume of carbon monoxide to the carbon monoxide electrolyzer 1705.

While the specification has been described in detail with respect to specific embodiments of the invention, it will be appreciated that those skilled in the art, upon attaining an understanding of the foregoing, may readily conceive of alterations to, variations of, and equivalents to these embodiments. The disclosure of volumes of chemicals in this disclosure is not meant to refer to a physically isolated volume as it is possible for a volume of dihydrogen to exist with a volume of carbon dioxide in a single physical volume. Although examples in the disclosure were generally limited to the integration of a CO electrolyzer and a chlor-alkali electrolyzer, the process chains disclosed herein do not require all the integrations described. For example, in the case of ethylene oxide production the source of the carbon monoxide or acid can be a different source and does not have to be a chlor-alkali electrolyzer. Although examples in the disclosure were generally applied to industrial chemical processes, similar approaches are applicable to chemical processing of any scale and scope. These and other modifications and variations to the present invention may be practiced by those skilled in the art, without departing from the scope of the present invention, which is more particularly set forth in the appended claims.

What is claimed is:

1. A method comprising:
generating a volume of chlorine gas using a chlor-alkali reactor;
generating a volume of dihydrogen using a carbon monoxide electrolyzer;
separating the volume of dihydrogen from an output stream, including an electrolyte, of the carbon monoxide electrolyzer;
generating a volume of hydrochloric acid using a hydrochloric acid reactor, the volume of dihydrogen, and the volume of chlorine gas;
acidifying the output stream of the carbon monoxide electrolyzer using the volume of hydrochloric acid;
converting, via the acidifying, a metal hydroxide in the output stream into a volume of a metal salt;
supplying the volume of the metal salt to the chlor-alkali reactor;
generating a volume of the metal hydroxide using the volume of the metal salt and the chlor-alkali reactor; and
supplying the volume of the metal hydroxide to the carbon monoxide electrolyzer to be used as the electrolyte.

2. The method of claim 1, wherein:
(i) the output stream includes a volume of carboxylates; and (ii) the acidifying of the output stream converts the volume of carboxylates to a volume of carboxylic acid.

3. The method of claim 1, further comprising:
generating a volume of acetate using the carbon monoxide electrolyzer and a volume of carbon monoxide;
monitoring a rate of production of the acetate; and
changing a rate of production of the volume of hydrochloric acid based on the rate of production of the acetate, wherein the rate of production of the volume of hydrochloric acid is increased when the rate of production of the acetate increases, and wherein the rate of production of the volume of hydrochloric acid is decreased when the rate of production of the acetate decreases.

4. The method of claim 3, further comprising:
supplying a first portion of the volume of dihydrogen to the chlor-alkali reactor;
wherein: (i) the generating of the hydrochloric acid uses a second portion of the volume of dihydrogen; and (ii) the changing of the rate of production of the volume of hydrochloric acid includes changing the first portion relative to the second portion.

5. The method of claim 4, further comprising:
capturing a first portion of the volume of chlorine gas;
wherein: (i) the generating of the volume of hydrochloric acid uses a second portion of the volume of chlorine gas; and (ii) the changing of the rate of production of the volume of hydrochloric acid includes changing the first portion of the volume of chlorine gas relative to the second portion of the volume of chlorine gas.

6. The method of claim 1, further comprising:
separating, using a liquid-gas separator, the volume of dihydrogen into a gaseous output stream from the output stream of the carbon monoxide electrolyzer; and
separating, using a gas separator, the volume of dihydrogen from the gaseous output stream.

7. The method of claim 6, further comprising:
separating, using the gas separator, a volume of ethylene from the gaseous output stream;
generating a volume of ethylene dichloride using an ethylene chlorination reactor, the volume of hydrochloric acid, and the volume of ethylene; and
generating a volume of vinyl chloride using an ethylene dichloride to vinyl chloride reactor and the volume of ethylene dichloride.

8. The method of claim 7, further comprising:
separating, a second volume of hydrochloric acid from an output stream of the vinyl chloride reactor;
wherein: (i) the output stream of the carbon monoxide electrolyzer includes a volume of carboxylates; and (ii) the acidifying of the output stream of the carbon monoxide electrolyzer converts the volume of carboxylates to a volume of carboxylic acid.

9. The method of claim 7, further comprising:
separating a second volume of hydrochloric acid from an output stream of the vinyl chloride reactor.

10. The method of claim 1, wherein:
the output stream includes a volume of carboxylates;
the acidifying of the output stream converts the volume of carboxylates to a volume of carboxylic acid; and
the method further comprises: distilling a volume of acetic acid from the volume of carboxylic acid; and
generating a volume of vinyl acetate using a vinyl acetate synthesis reactor, the volume of acetic acid, a volume of ethylene, and a volume of oxygen.

11. A method comprising:
generating a volume of a metal hydroxide and a volume of chlorine gas using a metal salt and a chlor-alkali reactor;
generating an output stream using a volume of carbon monoxide and a carbon monoxide electrolyzer, wherein the volume of metal hydroxide is an electrolyte of the carbon monoxide electrolyzer;
supplying the volume of metal hydroxide to the carbon monoxide electrolyzer to be used as the electrolyte of the carbon monoxide electrolyzer;
generating a volume of dihydrogen using the carbon monoxide electrolyzer;
separating the volume of dihydrogen from the output stream of the carbon monoxide electrolyzer;
generating a volume of hydrochloric acid using a hydrochloric acid reactor, the volume of dihydrogen, and the volume of chlorine gas;
acidifying the output stream of the carbon monoxide electrolyzer using the volume of hydrochloric acid, wherein the output stream includes the electrolyte;
converting, via the acidifying, a metal hydroxide in the output stream into a volume of the metal salt; and
supplying the volume of the metal salt to the chlor-alkali reactor.

12. The method of claim 11, whereby:
the output stream includes a volume of carboxylates; and
the acidifying of the output stream converts the volume of carboxylates to a volume of carboxylic acid.

13. The method of claim 12, further comprising:
generating a volume of acetate using the carbon monoxide electrolyzer and the volume of carbon monoxide; and
changing a rate of production of the volume of hydrochloric acid based on a rate of production of the acetate, wherein the rate of production of the volume of hydrochloric acid is increased when the rate of production of the acetate increases, and wherein the rate of production of the volume of hydrochloric acid is decreased when the rate of production of the acetate decreases.

14. The method of claim 13, wherein:
the generating of the volume of dihydrogen uses the volume of carbon monoxide;
the method further comprises supplying a first portion of the volume of dihydrogen to the chlor-alkali reactor;
the generating of the hydrochloric acid uses a second portion of the volume of dihydrogen; and
the changing of the rate of production of the volume of hydrochloric acid includes changing the first portion relative to the second portion.

15. The method of claim 14, further comprising:
capturing a first portion of the volume of chlorine gas;
wherein: (i) the generating of the hydrochloric acid uses a second portion of the volume of chlorine gas; and (ii) the changing of the rate of production of the volume of hydrochloric acid includes changing the first portion of the volume of chlorine gas relative to the second portion of the volume of chlorine gas.

16. The method of claim 11, further comprising:
separating a volume of ethylene from the output stream;
generating a volume of ethylene dichloride using an ethylene chlorination reactor and the volume of ethylene; and
generating a volume of vinyl chloride using an ethylene dichloride to vinyl chloride reactor and the volume of ethylene dichloride.

17. The method of claim 16, further comprising:
separating a second volume of hydrochloric acid from an output stream of the ethylene dichloride to vinyl chloride reactor.

18. The method of claim 11, further comprising:
generating a volume of oxygen using the carbon monoxide electrolyzer;
separating a volume of ethylene from the output stream; and
generating a volume of vinyl acetate using a vinyl acetate synthesis reactor, a volume of acetic acid, the volume of ethylene, and the volume of oxygen;
wherein: (i) the output stream includes a volume of carboxylates; (ii) the acidifying of the output stream converts the volume of carboxylates to a volume of carboxylic acid; and (iii) the volume of acetic acid is distilled from the volume of carboxylic acid.

19. A method comprising:
generating a volume of chlorine gas using a chlor-alkali reactor;
generating a volume of dihydrogen using a carbon monoxide electrolyzer;
separating the volume of dihydrogen from an output stream of the carbon monoxide electrolyzer;
generating a volume of acetate, in the output stream, using the carbon monoxide electrolyzer and a volume of carbon monoxide;
generating a volume of hydrochloric acid using a hydrochloric acid reactor, the volume of dihydrogen, and the volume of chlorine gas;
acidifying the output stream of the carbon monoxide electrolyzer using the volume of hydrochloric acid;
converting, via the acidifying, a metal hydroxide in the output stream into a volume of a metal salt;
converting, via the acidifying, the volume of acetate in the output stream into a volume of acetic acid;
separating the volume of the metal salt from the volume of acetic acid;
supplying the volume of the metal salt to the chlor-alkali reactor;
generating a volume of the metal hydroxide using the volume of the metal salt and the chlor-alkali reactor; and
supplying the volume of the metal hydroxide to the carbon monoxide electrolyzer to be used as an electrolyte.

20. The method of claim 19, wherein:
the generating of the volume of dihydrogen uses the volume of carbon monoxide;
the method further comprises supplying a first portion of the volume of dihydrogen to the chlor-alkali reactor and changing a rate of production of the volume of hydrochloric acid;
the generating of the volume of hydrochloric acid uses a second portion of the volume of dihydrogen; and
the changing of the rate of production of the volume of hydrochloric acid includes changing the first portion relative to the second portion.

21. The method of claim 19, further comprising:
capturing a first portion of the volume of chlorine gas; and
changing a rate of production of the hydrochloric acid;
wherein: (i) the generating of the hydrochloric acid uses a second portion of the volume of chlorine gas; and (ii) the changing of the rate of production of the volume of hydrochloric acid includes changing the first portion relative to the second portion.

22. The method of claim 21, wherein:
the generating of the volume of dihydrogen uses the volume of carbon monoxide.

23. The method of claim 19, further comprising:
generating a volume of chlorine gas using the chlor-alkali reactor;
separating a volume of ethylene from the output stream of the carbon monoxide electrolyzer;
generating a volume of ethylene dichloride using an ethylene chlorination reactor, the volume of chlorine gas, and the volume of ethylene; and
generating a volume of vinyl chloride using an ethylene dichloride to vinyl chloride reactor and the volume of ethylene dichloride.

24. The method of claim 23, further comprising:
separating a second volume of hydrochloric acid from an output stream of the ethylene dichloride to vinyl chloride reactor.

25. The method of claim 19, further comprising:
generating a volume of oxygen using the carbon monoxide electrolyzer;
separating a volume of ethylene from the output stream of the carbon monoxide electrolyzer; and
generating a volume of vinyl acetate using a vinyl acetate synthesis reactor, the volume of acetic acid, the volume of ethylene, and the volume of oxygen.

* * * * *